US011224382B2

(12) United States Patent
Reiner

(10) Patent No.: US 11,224,382 B2
(45) Date of Patent: Jan. 18, 2022

(54) METHOD AND APPARATUS FOR EMBEDDED SENSORS IN DIAGNOSTIC AND THERAPEUTIC MEDICAL DEVICES

(71) Applicant: Bruce Reiner, Berlin, MD (US)

(72) Inventor: Bruce Reiner, Berlin, MD (US)

(*) Notice: Subject to any disclaimer, the term of this patent is extended or adjusted under 35 U.S.C. 154(b) by 1001 days.

(21) Appl. No.: 15/434,783

(22) Filed: Feb. 16, 2017

(65) Prior Publication Data

US 2017/0231573 A1    Aug. 17, 2017

Related U.S. Application Data

(60) Provisional application No. 62/295,787, filed on Feb. 16, 2016.

(51) Int. Cl.
  *A61B 5/00* (2006.01)
  *A61B 8/12* (2006.01)
  *A61B 5/1473* (2006.01)
  *A61B 5/026* (2006.01)
  *A61M 5/142* (2006.01)
  *A61F 2/82* (2013.01)
  *A61B 5/0205* (2006.01)
  *A61B 5/07* (2006.01)
  *A61B 17/70* (2006.01)
  *A61M 5/172* (2006.01)
  *A61B 8/06* (2006.01)
  *A61F 2/01* (2006.01)

(52) U.S. Cl.
  CPC ............ *A61B 5/6861* (2013.01); *A61B 5/026* (2013.01); *A61B 5/073* (2013.01); *A61B 5/076* (2013.01); *A61B 5/1473* (2013.01); *A61B 8/06* (2013.01); *A61B 8/12* (2013.01); *A61B 17/7074* (2013.01); *A61F 2/82* (2013.01); *A61M 5/14244* (2013.01); *A61M 5/14276* (2013.01); *A61M 5/1723* (2013.01); *A61B 5/0205* (2013.01); *A61B 2562/046* (2013.01); *A61F 2250/0096* (2013.01)

(58) Field of Classification Search
  CPC .......... A61B 17/7074; A61B 2562/046; A61B 5/0205; A61B 5/026; A61B 5/073; A61B 5/076; A61B 5/1473; A61B 5/6861; A61B 8/06; A61B 8/12; A61F 2250/0096; A61F 2/01; A61F 2/82; A61M 5/14244; A61M 5/14276; A61M 5/1723
  See application file for complete search history.

(56) References Cited

U.S. PATENT DOCUMENTS

| | | | |
|---|---|---|---|
| 5,596,988 A * | 1/1997 | Markle | A61B 5/14539 600/353 |
| 9,895,103 B2 * | 2/2018 | Hyde | A61B 5/6887 |
| 10,959,878 B2 * | 3/2021 | Wolfertz | A61M 25/0045 |

(Continued)

*Primary Examiner* — Roy Y Yi
*Assistant Examiner* — Geoffrey T Evans
(74) *Attorney, Agent, or Firm* — Edwards Neils LLC; Jean C Edwards

(57) ABSTRACT

The present invention relates to miniature biosensor technology which can be directly embedded into medical device technology to create a new category of multifunctional smart medical devices. The resulting data from these smart medical devices results in wireless communication networks and standardized referenceable databases, which are used in the creation of best practice guidelines, clinical decision support tools, personalized medicine applications, and comparative technology assessment.

9 Claims, 8 Drawing Sheets

(56) References Cited

U.S. PATENT DOCUMENTS

| | | | |
|---|---|---|---|
| 2010/0198048 A1* | 8/2010 | Togawa | A61B 8/445 |
| | | | 600/411 |
| 2016/0029952 A1* | 2/2016 | Hunter | A61F 2/4657 |
| | | | 623/22.17 |
| 2017/0020422 A1* | 1/2017 | Bigelow | A61B 5/02042 |
| 2017/0068792 A1* | 3/2017 | Reiner | A61B 5/0022 |

* cited by examiner

METHOD AND APPARATUS FOR EMBEDDED SENSORS IN DIAGNOSTIC AND THERAPEUTIC MEDICAL DEVICES

CROSS-REFERENCE TO RELATED APPLICATIONS

The present invention claims priority to U.S. Provisional Patent Application No. 62/295,787, filed Feb. 16, 2016, the contents of which are herein incorporated by reference in their entirety.

BACKGROUND OF THE INVENTION

1. Field of the Invention

A medical device is defined as an instrument, apparatus, implant, in vitro reagent or similar article that is used to diagnose, prevent, or treat disease, without its intended purpose through chemical reaction or metabolism. While medical device technologies are extremely diverse in nature, the present invention is directed to surgical and medical instruments (e.g., vascular catheter or stent, spinal fixation device), which are primarily utilitarian in nature. In the course of the use of these instruments, they function to perform a specific and narrowly focused task (e.g., vascular access, spine stabilization), which is largely analyzed in gross and binary terms. For example, does the vascular stent maintain arterial patency (i.e., its primary intended purpose) and does it perform its purpose without the presence of complicating factors (e.g., infection)?

With the advent of miniaturized biosensors and nanotechnology, a new innovation opportunity is created to integrate sensor functionality into existing medical devices for the intended purpose of creating, recording, and analyzing medical data in vivo. This, in theory, creates an opportunity to expand the existing "static" functionality of medical devices into "dynamic" devices which can perform a number of additional functions above and beyond their current role. A vascular stent placed could not only maintain arterial patency but also continuously monitor its surrounding environment to assess structural integrity of the stent (e.g., leakage), flow characteristics (e.g., directionality, velocity), cellular physiology (e.g., platelet aggregation in the formation of thrombus), and chemistry (e.g., cytokines related to infection). The additional knowledge gained by this continuous collection and analysis of standardized in vivo data not only creates new found knowledge of device performance, but also provides a valuable means for early intervention, in the event of device malfunction or concomitant pathology.

2. Description of the Related Art

Recent advances in biomedical engineering have led to the creation of miniaturized biosensors (i.e., micro or miniature total analysis systems), and commonly referred to as "lab on a chip" devices. These miniaturized biosensors provide a number of advantages when applied to in-vivo medical monitoring including reduced size, small sample volumes, multi-analyte detection, reduced analysis time, reduced reagent use, and high uniformity. These advanced tools for studying cellular physiology and pathology are required by the medical community in order to advance disease diagnosis and treatment, which is not achievable by traditional methods.

The current state of the art in miniaturized medical biosensors involve micro-electro-mechanical systems (MEMS), which are mechanical and electromechanical elements developed through microfabrication techniques. MEMS technologies have rapidly progressed over time to currently establish a wide range of small high performance and inexpensive sensors able to detect and respond to a wide array of physical variables including (but not limited to) pressure, position, motion, strain, radiation, and flow. MEMS sensors can be integrated with information and communication technologies to create wireless communication and sensor networks; enabling the creation of compact, high performance, low power, low cost solutions for a wide range of applications. Another key feature of MEMS technology is the ability to merge quantitative measurements with embedded intelligence.

In recent years, Biomedical or Biological Micro-Electro-Mechanical Systems (BioMEMS) have shown a number of promising potential clinical applications related to advanced diagnosis, therapy, and tissue engineering. In the area of biomolecular analysis, BioMEMS provide an opportunity for sensing microorganisms, DNA strands, molecules, viruses, and cells. Motion sensors (e.g., accelerometers and gyroscopes) can be used in the analysis of motor impairment disorders (e.g., Parkinson's disease), to provide objective analysis of motion abnormalities, which can in turn be used for enhanced diagnosis and treatment assessment. BioMEMS have also been used for advance tissue engineering applications. Examples include complementary metal-oxide semiconductor (CMOS) compatible MEMS technology targeting label-free selective detection of biomolecules (i.e., specific RNA sequences); and BioMEMS device (based on a silicon dioxide-silicon nitride structure) used for testing mechanical properties of living cells.

To date, the primary focus of BioMEMS in medicine have focused on the monitoring of chronic disease (e.g., hypertension, obesity, COPD, diabetes, heart failure). While still in its infancy, the estimated market for MEMS sensors in medical disease monitoring and diagnosis is forecast to reach 6 billion dollars by 2018.

Thus, a way of combining miniature biosensor technology with medical device technology to create a new category of multifunctional smart medical devices using wireless communication networks and standardized referenceable databases, which can be used in the creation of best practice guidelines, clinical decision support tools, personalized medicine applications, and comparative technology assessment, is needed.

SUMMARY OF THE INVENTION

The present invention illustrates how miniature biosensor technology can be directly embedded into medical device technology to create a new category of multifunctional smart medical devices. The resulting data from these smart medical devices results in wireless communication networks and standardized referenceable databases, which are used in the creation of best practice guidelines, clinical decision support tools, personalized medicine applications, and comparative technology assessment.

The present invention relates to a medical device including: a biosensor having a plurality of embedded sensors disposed in at least an outer and inner wall of the biosensor; wherein the biosensor is disposed in a body of a patient; and wherein the plurality of embedded sensors include at least one of a diagnostic sensor or a therapeutic sensor.

In one embodiment, the diagnostic sensor records data with respect to at least one of a structural integrity of the biosensor, chemical or cellular data, flow dynamics, or ultrasound data.

In one embodiment, the medical device further includes: a reservoir disposed between the inner and the outer wall of the biosensor.

In one embodiment, the therapeutic sensor records data with respect to contents of the reservoir.

In one embodiment, the biosensor includes a plurality of biosensors at one or more ends of the biosensor.

In one embodiment, the biosensor is one of mobile or fixed.

In one embodiment, the biosensor wirelessly communicates data from at least one of the therapeutic sensor or the diagnostic sensor to at least one external data receiving device.

In one embodiment, the data is stored in a database of at least one external data receiving device.

In one embodiment, the medical device further includes: a needle which accesses the reservoir.

In one embodiment, the medical device further includes: an external pump; and an external reservoir.

In one embodiment, the medical device further includes: a guidance locking system disposed in an outer wall of said biosensor.

In one embodiment, the biosensor is at least one of a catheter or a stent.

In one embodiment, the data is recorded in real time.

In one embodiment, the external data receiving device is at least one of a handheld storage device or a computer system.

In one embodiment, a method of collecting and recording data from at least one biosensor disposed in a body of a patient, including: providing a plurality of sensors embedded in an inner wall and an outer wall of the biosensor; collecting data from the plurality of embedded sensors and wirelessly transmitting the data to at least one external data receiving device for recordation in a database of at least one external data receiving device; and creating a data profile for each of the embedded sensors.

In one embodiment, the data is recorded in real time.

In one embodiment, the external data receiving device is at least one of a handheld storage device or a computer system.

In one embodiment, the method further includes: recording pre-existing patient or technology risk factors or concomitant disease information in the database and correlating the risk factors or disease information with the data from the embedded sensors.

In one embodiment, the method further includes: determining abnormalities in the data and instituting analysis of the data to confirm the data abnormalities.

In one embodiment, the method further includes: repeating data collection of the data abnormalities and correlating the data abnormalities with comparable measurements from neighboring sensors.

In one embodiment, the repeated data collection measurements are abnormal, performing a quality assurance test of sensor reliability.

In one embodiment, the method further includes: instituting an automated notification with increased data surveillance, when the data abnormalities are confirmed.

In one embodiment, the method further includes: recording all verified communication responses received within a defined period of time, from end users receiving the automated notification, in the database for at least one of analysis or intervention response.

In one embodiment, the method further includes: performing analytics on the data recorded in the database, to correlate data outliers and the data abnormalities with comparable data over time, to create a time-activity curve which is used for decision support and comparative data analysis on other patients.

In one embodiment, the method further includes: cross-referencing a magnitude and type of the data outliers, technology in use, and location of the embedded sensors, with comparable data, in order to create a computerized predictor of disease probability, severity, and intervention response requirements.

In one embodiment, the method further includes: informing end users of an optimal intervention response upon receipt of the data abnormalities and the data analytics.

In one embodiment, the method further includes: customizing the optimal intervention response to the data abnormalities with respect to clinical or technical concerns, including specific patients, clinical contexts, or technology in use.

In one embodiment, the method further includes: employing an intervention strategy and monitoring for success or failure of intervention strategy by continuous data measures.

In one embodiment, the method further includes: recording data from the embedded sensors in the database for purposes of continuous patient and biosensor monitoring, outcomes analysis, and technology assessment.

In one embodiment, the method further includes: creating best practice guidelines using data analytics, which is specific to technology used and patient profiles.

Thus, has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to how miniature biosensor technology can be directly embedded into medical device technology to create a new category of multifunctional smart medical devices. The resulting data from these smart medical devices results in wireless communication networks and standardized referenceable databases, which are used in the creation of best practice guidelines, clinical decision support tools, personalized medicine applications, and comparative technology assessment.

The Smart Medical Device

Figure 8:
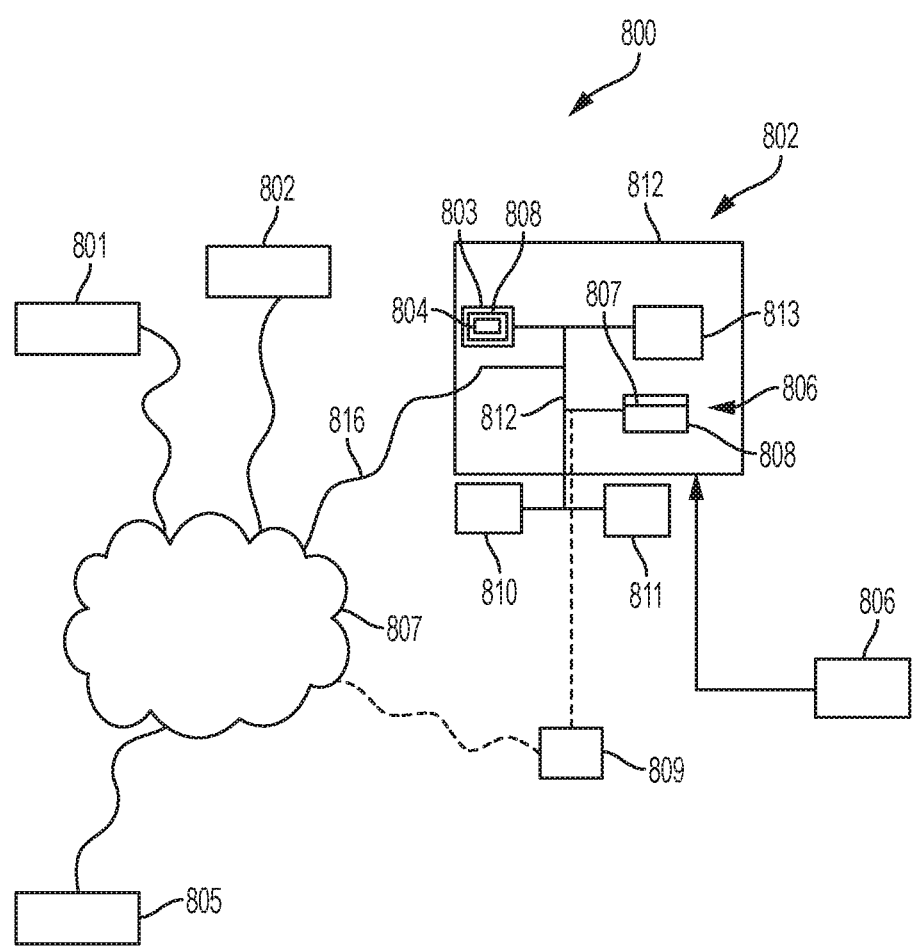
FIG. 8 is a schematic diagram of the data network of the present invention, according to one embodiment consistent with the present invention.

The "smart" medical device (e.g., catheter 100 of FIG. 1) is predicated upon the integration of MEMS sensors (e.g., sensors 101, 102), technologies, conventional medical devices, and everyday computer devices (e.g., smart phone 103, computer system 104) to create a multi-sensing and multimodal cloud framework. The computer system includes standard computer technology, such as a display, input mechanism (i.e., keyboard, mouse), and microprocessor which runs a program, and a memory in which a database of information is stored. The computer system may be hand-held, or may use both a hand-held and client computer and/or server, and may be wirelessly or hardwired to the smart medical device. (See also, FIG. 8 and description thereof, below).

The present invention enables the continuum and integrated management of a large number and variety of data which can collectively create a smart biologic ecosystem, which can be enhanced through the computational performance of microprocessors in computer systems 103, 104. The combined evolution and advancement in MEMS technologies and semiconductors can expand the purview and clinical applications of biosensors, data processing and analyses, and cost-efficacy and practicality of everyday use.

The creation of a "smart" medical device (i.e., catheter 100) using multifunctional embedded biosensors (i.e., sensors 101, 102) first requires the identification of different types of miniaturized sensor technologies which can be effectively integrated with the medical device of interest, determination of the data which will be created, method for wireless communication of the corresponding data with a handheld device 103 or computer system 104, creation of a referenceable database in a computer system 104 or server (not shown), of sensor-derived standardized data, methodology for secure access and communication of the data, creation of customizable data analytics, determination of "best practice" or evidence-based standards in accordance with the specific medical device, underlying clinical disease, and patient-specific attributes.

This collectively forms the basis of a "smart" diagnostic medical device (e.g., catheter 100), which effectively creates a method for continuous real-time data in vivo, which can be acted upon based on temporal analysis of data by a program running on the computer system 103, 104, over the lifetime of the medical device (i.e., catheter 100) along with early detection by the program of temporal change in the data. The continuous collection of data by sensors (i.e., sensors 101, 102) over the lifetime of the medical device (i.e., catheter 100) provides a means with which early temporal change in baseline data analyzed by the program can provide an early warning to the possibility of early pathology, as it relates to the medical device itself or the surrounding milieu in which it is positioned.

In addition to diagnostic capabilities, a sensor-driven smart medical device may also possess the ability to have therapeutic properties, through the ability to actively or passively intervene in relationship to the underlying pathology, based on the program. Active intervention may include actions which can be directly taken by the program of the smart medical device to treat the underlying pathology, while passive intervention may include the ability of the program of the smart medical device to directly interact (i.e., collaborate) with another device or entity to therapeutically intervene. Examples of both active and passive therapeutic medical devices are described herein.

In the present invention, the specific clinical applications and data requirements are identified for use with the "smart medical device" (i.e., catheter 100) using biosensors (i.e., sensors 101, 102). A wide array of clinical applications may be used with these smart medical devices including (but not limited to) early diagnosis of device malfunction, loss of device integrity, early diagnosis of disease, and a variety of device-driven therapeutic applications.

Embedding biosensors (i.e., sensors 101, 102) within the internal and external components of the medical device (i.e., catheter 100) effectively creates continuous data collection by the program, related to local physiology and/or medical device functionality/integrity. The present invention encompasses a variety of medical devices which demonstrate construction, functionality, data creation and analysis, provider/patient alerts and feedback, and intervention. While the present invention can be applied to hundreds of different types of medical devices, a number of illustrative examples of medical devices are discussed herein. The examples provided herein demonstrate the applicability of the present invention to the creation of smart medical devices throughout a much broader and extensive array of medical devices in everyday clinical use.

Device Specific Data

Figure 1:
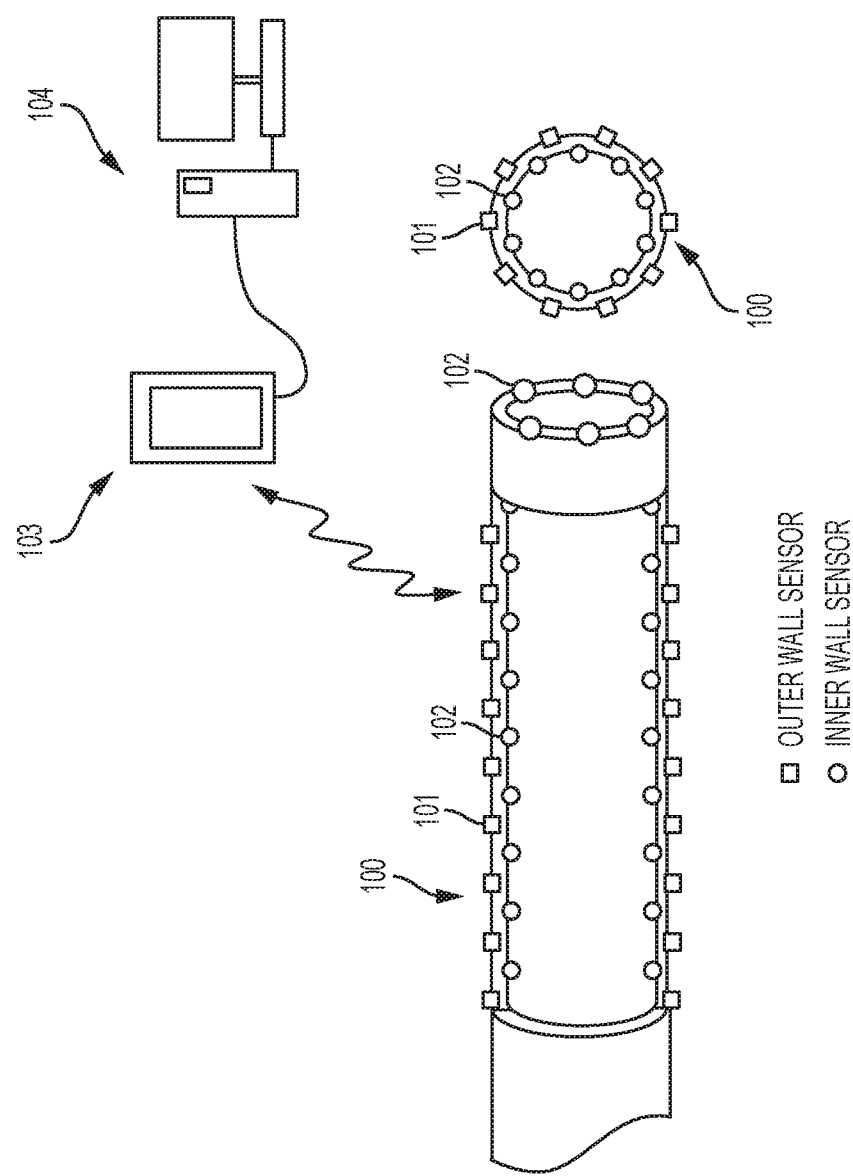
FIG. 1 is a schematic diagram of a side view and end view of a medical device, including a venous catheter with embedded sensors in its outer and inner walls and catheter tips, according to one embodiment consistent with the present invention.

In one embodiment as shown in FIG. 1, the smart medical device (i.e., catheter 100) is achieved by the integration of different types of biosensors (i.e., sensors 101, 102) directly into the construction of the medical device. The miniaturized embedded sensors do not routinely affect device functionality and/or structural integrity. The specific type of biosensors embedded within each different type of medical device is commensurate with the functionality of the device, its anatomic location, clinical condition (i.e., underlying disease in which it is being deployed), and potential complications associated with the specific medical device.

Figure 10:
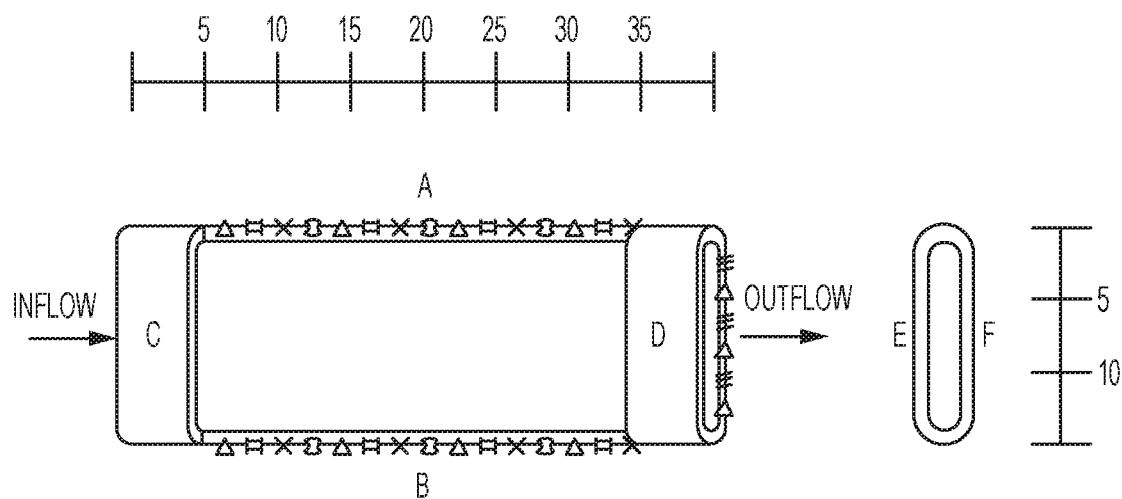
FIG. 10 is a schematic diagram of a biosensor specific structure, according to one embodiment consistent with the present invention.

To describe the sensors in more detail, FIG. 10 shows a representation of a number, location and functionality of individual sensors within each individual medical device, which can be visualized in the form of a device specific sensor roadmap. This can be issued in a standardized format by the device manufacturer, with electronic links of individual sensor-specific data to the central medical device database. In FIG. 10, which shows an exemplary vascular catheter, five different types of sensors are contained within the device, four of which are diagnostic (i.e., structural integrity, flow characteristics, and detection of local cells/chemicals), and one of which is therapeutic (i.e., drug storage and release). In addition to identifying individual sensors based upon their type and functionality, each individual sensor can be localized on the basis of a standardized numerical wall distribution grid. Knowledge of individual sensor location can assist in a variety of functions including detection of focal pathology, device structural defects, sensor quality control (i.e., detection of individually malfunctioning sensors), and localized guidance of therapy.

Turning back to FIG. 1, this figure illustrates a variety of sensor derived data requirements for a medical device—i.e., venous catheter 100. The specific data requirements can be further specialized in relation to the specific catheter type and complications of highest concern. FIG. 1 includes: Sensor Derived Medical Device Data Requirements (Venous Catheter 100), such as:

A. Vascular Flow
  1. Input and Output Flow Rates and/or Pressure Measurements
  2. Directionality
  3. Velocity
  4. Viscosity
  5. Turbulence
B. Cell Composition and Chemistry
  1. Morphology
  2. Histology
  3. Size
  4. Local Chemistry
C. Structural Integrity
  1. Porosity
  2. Diffusion
  3. Cross Flow
  4. Defect (size and number)
  5. Thickness
  6. Breakage (partial or complete)

As an example, if infection is a high priority complication, the program will direct the sensors 101, 102 in the outer and inner walls, respectively, and catheter 100 tips, to retrieve data focused on the detection of infection related cells (e.g., leukocytes) and chemistries (e.g., cytokines, reactive oxygen species). Similarly, if the complication of thrombus is of primary concern, the focus of the program will shift to thrombus related cells (e.g., platelets) and chemistries (e.g., thromboxanes). The local sensor 101, 102 derived data from the medical device 100 can be correlated by the program with generalized medical data to enhance diagnostic accuracy and determination of systemic response. In the example of localized device infection, the device specific metrics (e.g., leukocyte migration, cytokine measurements) can be correlated by the program with systemic clinical data (e.g., white blood cell count, body temperature) to assist in diagnostic accuracy as well as determine the impact of the localized infection on overall body measures.

If the device 100 is changed from that of a venous catheter to an arterial catheter, then flow pressure measurements and gradients would take on a high priority, which is not the case with a venous catheter. This illustrates how specific device type and anatomic location play a fundamental role in determining the data device requirements of highest priority. At the same time, requirements for assessment of device structural integrity may highly vary in accordance with device type, anatomic location, and functionality. A single lumen venous catheter 100 may have low rates of structural integrity concerns and when present, may be largely restricted to the ends of the catheter. As a result the number and distribution of sensors 101, 102 specific to structural integrity data may be limited.

On the other hand, a venous filter may have a higher rate of breakage thereby requiring a far greater number of sensors specific to device integrity analysis. Knowing that breakage tends to be most common among the struts of this device would result in the distribution of these sensors to the specific device location of highest concern. This same analogy can be drawn to a number of other types of medical devices (e.g., cardiac pacemaker, orthopedic prosthesis). By knowing the statistical likelihood and location of a device-specific complication, the number, distribution, and specific types of sensors can be customized in a manner to most effectively and accurately assess device functionality, integrity, and underlying disease.

While assessment of flow related data by the program may be of high priority to vascular medical devices (e.g., catheters, stents, filters), it would not be a primary concern to fixed medical devices within static tissues or organ systems. An orthopedic prosthesis situated within a skeletal structure (e.g., hip prosthesis) would have no concern for physiologic flow or movement based upon its anatomic location and functionality. On the other hand, one of the primary complications associated with a hip prosthesis is abnormal movement of the prosthesis from its normally fixed position (which may be exacerbated by specific types of stressors or bodily movements). This type of device translational motion may be recorded by specific sensors (e.g. gyroscopic, motion sensors) positioned in the distal (i.e., femoral) tip of the prosthesis which is most prone to abnormal movement, and analyzed by the program. Since baseline and continuous data is collected and stored in the computer system 103, 104 database, newly collected data by the program can be compared to identify subtle temporal data changes. The ability to continuously collect real-time data in the database also provides the program with the ability to analyze and differentiate a transient data outlier from that of a repeated and substantiated data abnormality. The longitudinal nature of sensor derived data also provides important insights as to the degree of the data abnormality as well as its rate of change. This data can be cross referenced by the program with large sample sized statistics to determine the optimal course of intervention. In this example of the hip prosthesis which has recently been shown to demonstrate 2 mm of movement at its distal tip, one would need to address the following using the program:

1. Is the measure degree of abnormal movement (i.e., 2 mm) severe enough to require immediate intervention or can it be conservatively managed?

2. To what extent is the rate of change in movement over time impact clinical decision making?

3. How does the patient's underlying attributes (e.g., age, weight, mobility) impact the decision of intervention options?

4. Does this specific type of prosthesis (i.e., manufacturer, model) have any unique data attributes and/or outcome measures relative to its peers?

The sensor derived data can also be correlated by the program with relevant external data in order to analyze it and assist the clinician in diagnosis and treatment planning. In the example of the hip prosthesis with early detection by the program of abnormal motion due to prosthesis loosening, dynamic response of the sensor derived data measures with positional/activity change may prove valuable in the assessment of clinical severity and optimal treatment planning. If for example, the sensor derived prosthesis movement is exacerbated at a specific point in time relative to its baseline measure, the question is what was the precipitating cause for this sudden worsening in prosthesis movement? By the program correlating the sensor derived data with an analysis of patient activity, one can effectively learn what specific changes in positioning or activity of the patient exacerbated the pre-existing device deficiency.

In addition, if conservative management is chosen (e.g., physical therapy), the program can identify the objective response of prosthesis motion to the intervention, and what specific exercises were the most instrumental in increasing or decreasing the sensor derived motion data. The ability of the program of the present invention to correlate medical device and other forms of patient data may assist in diagnosis and treatment planning.

Additional subjective data elements (e.g., subjective pain) may also prove to be of value when the program correlates it with sensor derived data. If for example, the patient's subjective sensation of hip pain is found by the program to correlate with sensor derived motion measurements, one can ask the patient to keep a log or journal of day to day activity and subjective pain measures (with corresponding times). This patient log can in turn be analyzed by the program to correlate with the objective device derived data to determine the correlation between daily activities, subjective pain, and device motion.

An alternative application may include a periodic prompt or alert by the program to the patient inputting a record of activity or pain at a specific point in time when corresponding device related data is recorded by the program in the database (i.e., an unexpected increase in device motion). The patient could input this data into the computer system 103, 104 in a variety of methods (e.g., speech, text), which would be automatically entered into the device database for future analysis.

If the data is recorded by the program into the database, in a standardized format (e.g., standardized pain score on a 1-5 scale), this referenceable database can encompass large numbers of patients, medical devices, and clinical conditions. This provides the ability of the program to perform large sample size statistical analysis, which is important for determination of evidence based medicine (EBM) practice guidelines and best practice standards.

At the same time, one can take into account patient specific attributes so that the program can determine optimal treatment strategies and options specific to both the device and patient. As an example, a patient who is morbidly obese may have higher risk of hip prosthesis revision failure then a patient of smaller size. As a result, the criteria for removal of the prosthesis and revision may be higher than that of a normal sized patient (e.g., 5 mm instead of 3 mm). This illustrates how sensor derived smart medical device data (and the derived referenceable database), clinical diagnosis, decision making, and treatment options can be customized by the program to the specific medical device, patient, and pathology in question.

The determination of sensor distribution, number, and type (i.e., sensor deployment) are routinely determined by the specific type if device, functionality, and anatomic location. However, in some circumstances there may be the need to customize sensor deployment in accordance with the individual patient or clinical situation. Taking the prior example of a hip prosthesis, an example of two different patients who are planning to have hip replacement surgery is considered. One patient is of normal body size (e.g., 5 foot 6 inches, 160 pounds), while the other patient is morbidly obese (e.g., 5 foot 6 inches 320 pounds). Using the program to create statistics from the device database, the program determines that morbidly obese patients have a three times greater risk of failure due to prosthesis breakage and/or motion at the distal (i.e., femoral) end of the prosthesis. Having this added knowledge, the surgeon may elect to select a prosthesis which has designed with a greater number of motion/integrity sensors in its distal end than most of its counterparts; thereby, having a greater likelihood of success of early detection of abnormal motion and/or device breakage.

This is an example of how medical device sensor deployment can be customized in accordance with the specific patient and/or clinical situation, in order to improve the accuracy of sensor derived data and clinical outcomes. This essentially elevates the concept of a "smart" medical device to that of a "smarter" medical device, by customizing sensor deployment and data collection/analysis specific to the individual patient and clinical context.

A similar analogy can be made with the patient who is having a central venous catheter placed for venous access, and has a long history of repeated catheter induced venous thrombosis. Having this additional knowledge in hand, the venous catheter selected by the clinician using the program analytics, should have sensor deployment to optimize early detection of thrombus. In this example, a venous catheter may be selected with greater sensor number and/or higher sensitivity to thrombus related data (e.g., detection of fibrin, platelet aggregation, prostaglandins, and thromboxanes).

Sensor derived data (from different types of sensors) within a given medical device can often be complementary or synergistic in nature. In the prior example of the hip prosthesis which was found to have abnormal motion, this provided an important early alert which the program can send by electronic means (i.e., email, fax, text, etc.) to both the provider and patient of prosthesis malfunction. Knowing that abnormal prosthesis motion is often seen in association with underlying infection, it is important for the program to assess neighboring sensors specific to infection related data. If sensor deployment has been done so as to position both types of sensors in proximity to one another, this would allow for correlation by the program of both types of data in the hopes of maximizing both the sensitivity and specificity of the underlying data. This is important from a clinical standpoint, since the addition of infection (to the identified motion abnormality) may have a significant effect on treatment options and strategy. At the very least the presence of infection would necessitate antibiotic therapy and at the most may require prosthesis removal and complete clearance of the infection prior to prosthesis replacement.

While routine sensor related diagnosis of infection (based upon local cellular and chemical analysis), by the program, may require a certain data threshold, this may be modified by the program when a high risk factor or infection is documented (e.g., 2 mm prosthesis motion). Modification may include lowering the requisite data requirements, increasing data vigilance (e.g., more frequent data collections), or even introducing additional data sources.

Figure 2:
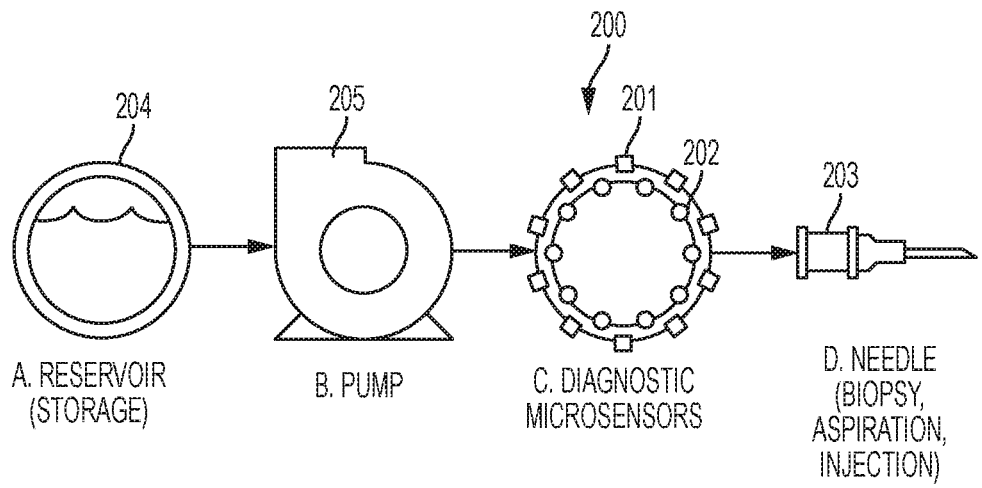
FIG. 2 is a schematic diagram of a medical device system, including a biosensor with embedded sensors, a needle, pump and reservoir, according to one embodiment consistent with the present invention, according to one embodiment consistent with the present invention.

If for example, as shown in FIG. 2, a sensor 200 with biopsy or aspiration capabilities (e.g., microfluidic sensor 201, 202 for diagnosis, with microneedle 203 for biopsy, aspiration or injection, reservoir 204 for storage, and micropump 205 for providing energy for needle 203 deployment and function) was incorporated into the prosthesis, one could obtain a small aspirate using the needle 203 in the region of interest which can be analyzed and cultured.

When the needle 203 is deployed for aspiration or biopsy, the specimen obtained is transferred to the reservoir 204 for short term storage. The specimen can in turn be expelled from the reservoir 204 through the needle 203 into a specimen collection device (not shown). Similarly, when the needle 203 is used for drug delivery, the chemical compound to be delivered is transferred from the reservoir 204 to the needle 203, where it is then discharged. This illustrates the two-directional flow capabilities of the reservoir 204 and needle 203 apparatuses, which are in turn provided power via the associated pump mechanism 205.

(A specific example of retrieving an aspirate is described below. The important point to be made is that sensor derived data can be used by the program, both independently and in combination with other sensor data, to improve data accuracy and early disease detection).

Multi-Device Data

Figure 3:
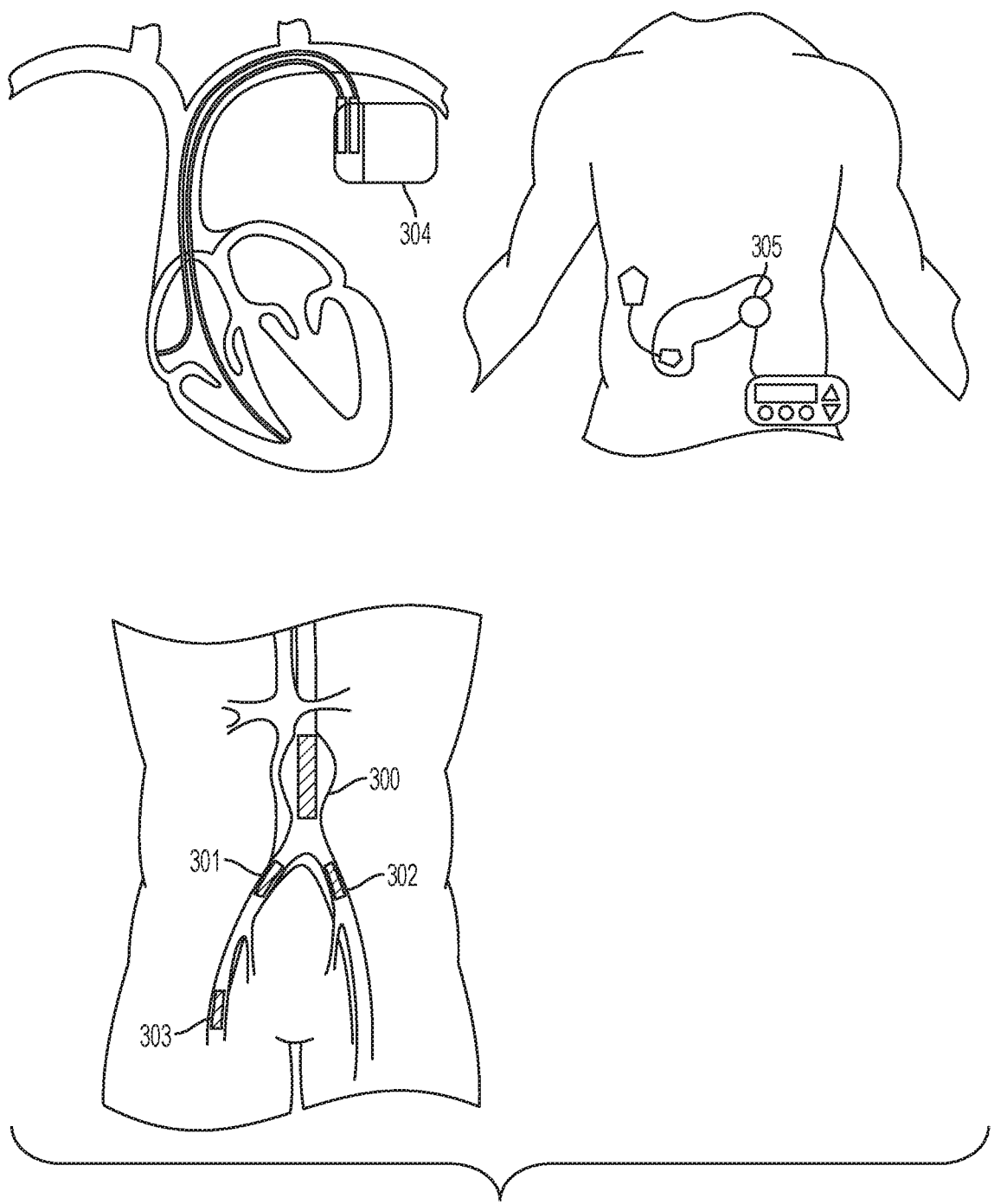
FIG. 3 is a schematic diagram of multi-medical device systems, including biosensors with embedded sensors in arterial stents, used with cardiac pacemakers or artificial pancreases, according to one embodiment consistent with the present invention.

In addition to sensor data from a single fixed medical device, in some circumstances, multiple medical devices may be present, which have the potential to synergistically improve diagnosis. In the example of an arterial stent (see FIG. 3, for example), one of the important sensor derived data is that of arterial pressure measurements at the proximal end of the stent, middle of the stent, and distal end of the stent. These combined pressure measurements produce a pressure gradient measurement which provides insight to the degree of stent patency (along with synchronous sensor data measuring flow directionality, velocity, viscosity, and turbulence). If the stent inflow arterial pressure is greater than the outflow arterial pressure measurement, as analyzed by the program, then the difference is the pressure gradient which corresponds to the degree of arterial stenosis. In the event that no arterial outflow is measured, this indicates occlusion of the stent.

When pressure and flow data of the arterial stent sensors is combined by the program with synchronous data from other medical devices (in the same patient and at the same time), the combined multi-device data may prove beneficial in providing valuable clinical information outside of the primary medical device location. Suppose, for example, the patient has four different arterial stents in the treatment of peripheral vascular disease. These stents (see FIG. 3) are located in the abdominal aorta (stent 300), right common iliac artery (stent 301), right superficial femoral artery (stent 303), and left common femoral artery (stent 302). Sensor derived measurements from the stent 301 in the right common iliac artery are analyzed by the program and show that the stent 301 is patent and has no significant change in velocity or pressure across its length. However, when the arterial inflow data (i.e., sensors in the proximal stent) is correlated by the program with data from the abdominal aortic stent 300 (which is proximal to the common femoral artery stent), then this data shows that there is a drop off in arterial pressure somewhere between the distal end of the abdominal aortic stent 300 graft and the proximal end of the right common femoral arterial stent 301. The severity of this obstruction can be further surmised based upon the degree of segmental pressure change between these two arterial stents 300, 301.

In a further step, if the pressure and velocity measurements between the right and left common femoral arterial stents 301, 302 are compared by the program, the result may be that the inflow measurements of the left common femoral artery stent 302 are comparable to the pressure/flow outflow measurements of the abdominal aortic stent 300 graft. These comparative device specific measures provide evidence that the obstruction occurs after (i.e., distal to) the aortic bifurcation and proximal to the right common femoral arterial stent 301, most likely at the origin of the right common femoral artery. If the obstruction had instead been located in the distal abdominal aorta (proximal to the aortic bifurcation), a comparable abnormality would have been expected in the left common femoral artery stent 302, which was not the case. At the same time, comparative pressure and flow inflow measurements in the right superficial femoral artery 303 stent, show no significant change in measurements when compared by the program to the right common femoral artery stent 301, which would mitigate against an obstruction in the arterial segment separating these two stents 301, 303.

One important application of the present invention shows how the device related measurements can be sequentially analyzed by the program to identify the timing, severity, location, and etiology of pathology. Using the same patient with four arterial stents 300-303 (in the treatment of peripheral vascular disease), the sensors capture a sudden and rapid change in arterial inflow measurements in the right common femoral artery stent 301, accompanied by complete absence of distal stent outflow. The program analysis indicates that an acute obstruction has occurred in the right common femoral artery stent 301, the specific location of which can be determined by the program analyzing neighboring sensor data along the course of the stent 301.

The two likely causes of pathology are progression in atherosclerotic plaque or embolism. Since the "pre-event" measures as analyzed by the program, showed a relatively mild degree of obstruction, and the abnormity occurred quite acutely (i.e., in the 15 minute interval of routine sequential measurements), the logical etiology is that of embolism. Since the embolism source can occur anywhere proximal to the point of obstruction it is often difficult to localize the exact source. However, in this case, analysis by the program of the data from the sensors in the internal wall of the abdominal aortic stent 300 graft, had previously demonstrated a significant burden of atherosclerotic plaque along the middle of the stent 300, which is no longer detected by the sensors. By calculating the distance between the sensors, and "before and after" sensor data, the program can estimate the size of the embolus (i.e., 2.5 cm), which correlates with the luminal diameter of the occluded right common femoral artery stent. Knowing the etiology, source, timing, and severity of this obstruction, allows the program to provide timely diagnosis, notification, and intervention. Having the ability of the program to correlate real-time data from multiple individual devices provides additional knowledge and insight not available when data is limited to that of a single medical device alone.

Using another example, suppose this same patient had an indwelling cardiac pacemaker 304 due to an underlying cardiac arrhythmia. Analysis derived from the pacemaker sensors, by the program, revealed a prolonged period of atrial fibrillation 24 hours prior to the event in question (i.e., embolic obstruction of the right common femoral artery stent 301). Since atrial fibrillation is a well-documented cause for cardiac thrombus formation and subsequent emboli, this could also serve as a source of the embolic disease. One method of differentiating between the two possible sources of emboli (i.e., cardiac versus abdominal aorta) is for the program to analyze the flow data derived from the abdominal aortic stent 300 graft data during the specific time frame of concern (i.e., the period of immediately preceding and up to the time the occlusion of the right common femoral artery stent 301 was identified). If, the thrombus had originated from the heart, then the embolus would have had to pass through the abdominal aortic stent 300 before passing into and obstructing the right common arterial stent 301 graft. This could have been identified by the program retrieving sensor derived data within the abdominal aortic stent 300 graft during the time in question, and evaluating for the presence of abnormal internal flow (e.g., loss of normal laminar flow, alteration in flow directionality, presence of an intraluminal mass separate from normal red blood cells). This last feature can be facilitated by incorporating ultrasound capabilities within the sensors, which provides the ability of the program to use ultrasound to analyze medical device internal flow and wall characteristics.

Therapeutic Applications

The present invention is not just used in diagnostic applications. In addition, the smart medical device 100/200 of the present invention also includes a number of therapeutic and interventional options, aimed at treating local disease and device malfunction. These therapeutic options take advantage of existing MEMS technology which is currently used in miniaturized drug delivery systems (artificial pancreas 305, for example), micropumps, activators, valves, reservoirs, and microneedles (see FIG. 2, for example). In addition to drug delivery, these systems can be used for blood/cell extraction, fluid sampling, cancer therapy, and cellular surgery. In the areas of biomolecular analysis and sensing, MEMS provide an opportunity for sensing microorganisms, DNA strands, molecules, viruses, and cells. This provides a number of potential applications related to early and advanced diagnosis, therapy, and tissue engineering that conventional medical devices have not reached. Thus, the integration of biosensors into medical devices provides a number of novel therapeutic applications.

Once the sensor derived medical device data has been validated and reproduced by the program (via longitudinal real time data collection and sensor quality control), a diagnosis is realized thereby. Therapeutic options are dependent upon a number of factors including (but not limited to) the severity and duration of the data abnormality, the clinical context, the type of medical device, and specific patient attributes. Since non- and less-invasive intervention is typically preferable, conservative management options will be employed by the program, if feasible. These medical device interventional strategies fall into three categories: local disease, device malfunction, and loss of device integrity.

A number of device-related medical complications and diseases may be identified by the program including (but not limited to) infection, thrombus, bleeding, tissue damage, and malignancy (which is not directly related to the device but instead the result of pre-existing disease). In these situations where pathology is intimately related or in direct proximity to the medical device, an opportunity arises to use the medical device as a vehicle for therapeutic intervention. Since pharmacologic therapy is an integral component of treatment for infection, thrombus, bleeding, and malignancy, medical device drug delivery represents one of the most important opportunities for medical device therapy. To date, a limited number of drug delivery applications have been developed using biosensor technology including, for example, microfluidic transdermal drug delivery. Similar technology using micropumps, microneedles, reservoirs, microflow sensors, and electronic circuitry, can be adapted for use in medical devices.

Figure 4:
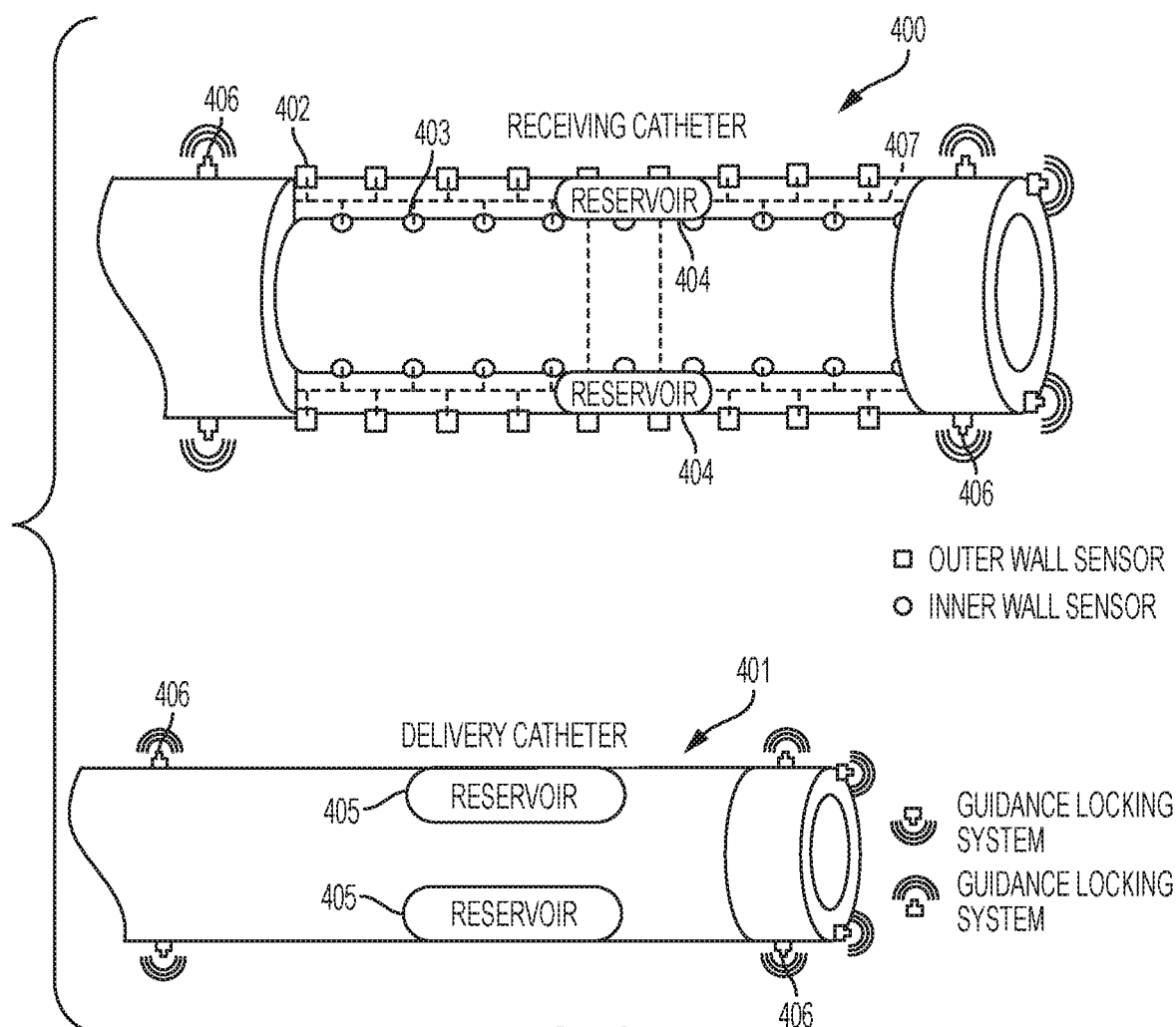
FIG. 4 is a schematic diagram showing a medical device system including a delivery catheter and a receiving catheter which provide a drug delivery system to an area of pathology, according to one embodiment consistent with the present invention.
Figure 5:
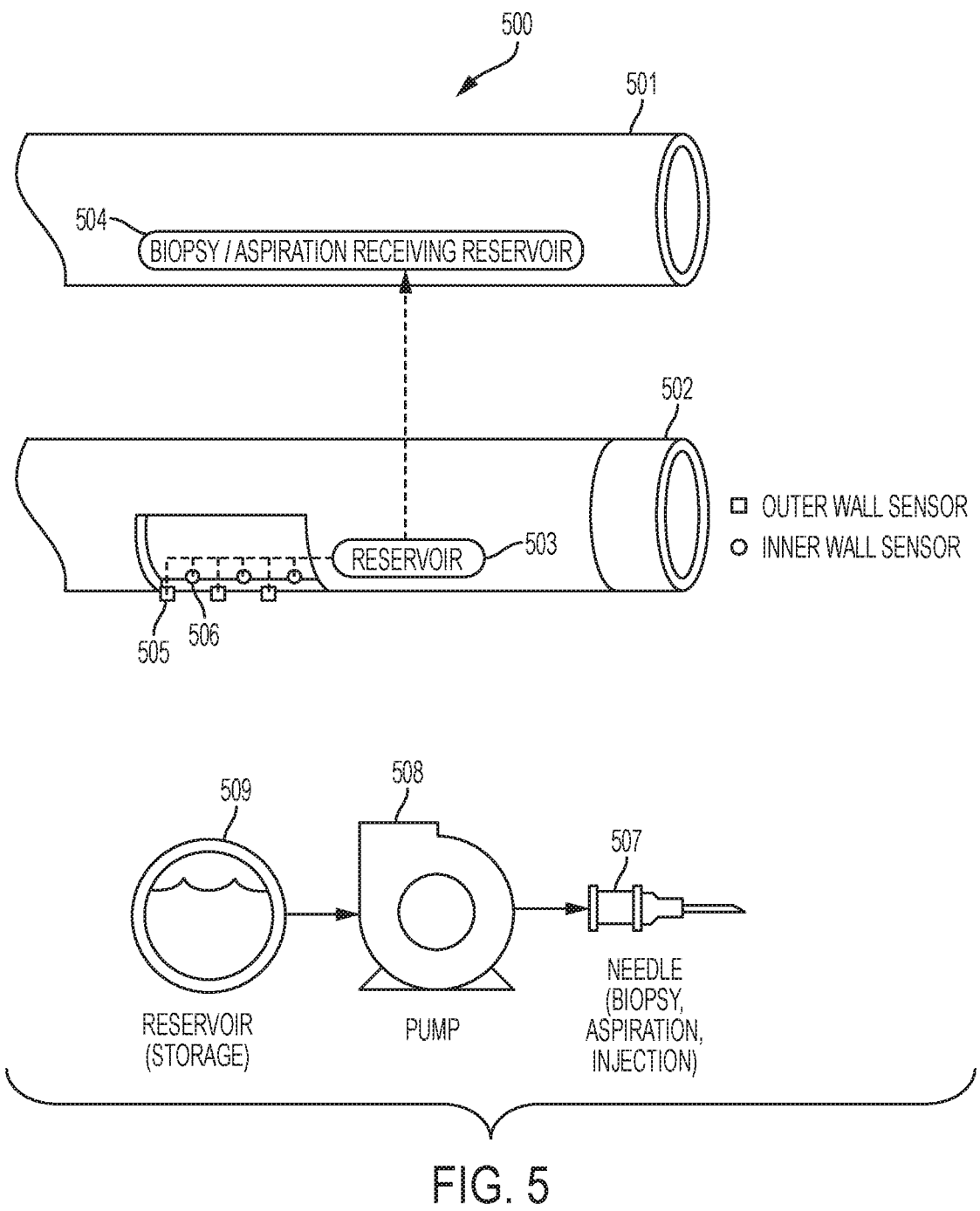
FIG. 5 is a schematic diagram showing a medical device system including a first biosensor with internal reservoir, and second biosensor with a receiving reservoir for biopsy or aspirated material from the first biosensor, and showing needle, pump and external reservoir, according to one embodiment consistent with the present invention.

FIGS. 2, 4 and 5 illustrate how sensor technology can be integrated into medical device (e.g., vascular catheter 200/400/500) for local drug delivery, which can be directly integrated with diagnostic sensor applications. This ability to combine diagnostic and therapeutic applications into a single device are unique to the present invention and create a "smart" medical device which can both diagnose and treat medical disease, as well as objectively measure the treatment response.

In the most simplistic application (see FIG. 2), and as described above, a catheter 200 is equipped with biosensors 201, 202 for the detection of thrombus, identifies the presence of early thrombus formation through the detection of localized cells (e.g., platelets) or chemical compounds (e.g., fibrin) along the outer walls of the catheter 200.

A number of diagnostic data can be recorded by these sensors 201, 202 including (but not limited to) the exact location of the thrombus, the volume of thrombus, the rate of growth, and the presence of superimposed pathology (e.g., infection) through DNA analysis and cellular/chemical assays. Once this data is recorded by the program in the database, a number of data distribution steps can take place. Firstly, the recorded data is automatically transmitted by the program to the device database (see for example, U.S. patent application Ser. No. 15/257,208, filed Sep. 6, 2016, on "System and Method for Medical Device Security, Data Tracking, and Outcomes Analysis", which is herein incorporated by reference). Once entered by the program into the device database, the new data is analyzed by the program (using artificial intelligence and rules based analyses) to determine whether additional action is required. If a predefined threshold is realized, the program performs a subsequent action to determine the importance and validity of the data abnormality. This may include repeating the data collection (to validate the initial data measurement), correlating the recent data measure with comparable historical data measurements (to differentiate between a new or pre-existing data trend), and cross referencing the new data measurement with larger data samples within the database from similar patients and medical devices. If the abnormal data is validated by the program and determined to exceed the predefined threshold of abnormalcy, an automated alert is transmitted by the program via electronic methods (i.e., text, fax, email, etc.), to authorized individuals (e.g., primary care physician, physician specialist, patient, family member), notifying them of the abnormal data measurement and requirement for formal acknowledgment and potential intervention.

Based upon this data review and analysis by the program, the clinical care provider may elect to initiate treatment commensurate with the type and severity of the data abnormality recorded. While systemic drug therapy is the current norm, this has a number of undesirable effects (e.g., organ toxicity, allergic reactions) related to the higher dose requirements of systemic therapy (as opposed to local therapy). Local therapy on the other hand offers the theoretical benefits of direct delivery of the therapy to the site of pathology (and earlier/improved therapeutic response), lower dose requirements, and decreased systemic effects of the drug being delivered.

The local drug delivery can be achieved by release of the therapeutic agent from drug reservoirs (see FIG. 4, reservoir 404, or see FIG. 5, reservoir 503, for example) which are directly embedded in the medical device in one embodiment (i.e., storage components 304, 504), rather than transported via micropumps which provide energy for needle deployment and function (see FIG. 2, needle 203 and pump 205, for example). The therapeutic agent can be administered to the specific site of pathology detection (i.e., determined by diagnostic sensors), and then released into the local site of pathology via a needle which is connected to the drug reservoir.

Alternatively, for example, reservoirs and microneedles can be directly incorporated into the system having diagnostic sensors, thereby allowing for local drug delivery without the need for a distributed drug delivery architecture. After the needle releases the pharmacologic agent into the local site of pathology, periodic measurements can be obtained by the diagnostic sensor to measure treatment response along with the need to modify therapy (e.g., adjust dose, change drug delivery timing, or change pharmacologic agent). A timing system can be integrated into the medical device to provide the ability to deliver drug doses at prescribed intervals or through continuous infusion. This ability to prospectively modify treatment (in real time) in accordance with continuous data measurements is a unique feature of the invention.

Since storage capacity of different pharmacologic agents is limited in accordance with the medical device size and architecture, an alternative strategy is the use of secondary medical devices 401 (see FIG. 4) for drug delivery to the primary medical device 400. This in effect is the equivalent to in-flight aerial refueling. The "delivery" catheter 401 is loaded with the desired pharmacologic agent and navigates itself to a position either alongside (i.e., in series) or on top of (i.e., in parallel) to the medical device 400 of interest. The ability to navigate one device 401 in proximity to another device 400 can be done through an internal tracking system which utilizes radiofrequency or Doppler technology (i.e., guidance system 406) to send out a signal (i.e., sound, light) for automated or mechanical guidance of the delivery device 401 to the primary medical device 400. Once these two devices 400, 401 are in proximity to one another a "docking system" is deployed, where external guiding mechanisms 406 in each of the catheters provide for physical alignment of the two catheters 400, 401 and their embedded sensors 402, 403, and which effectively connects the two devices 400, 401.

Once these devices 400, 401 are successfully aligned and connected to one another, the injection apparatus of the delivery catheter 401 is engaged, and the needle (not shown in FIG. 4) that is attached to the reservoir 405 of the delivery catheter, and is discharged and in turn, enters the receiving catheter 400 and reservoir 404. Once the two reservoirs 404, 405 are connected (via the delivery catheter needle), the contents of the delivery catheter 401 and reservoir 405 can be emptied from the delivery device 401, so that the pharmacologic agent is then delivered (via micropumps, not shown, but like pump 205 in FIG. 2) and conduits) to the reservoir 404 of the receiving catheter 400.

Once the transfer of reservoir 405 contents has been completed, the receiving catheter reservoir 404 can in turn transfer contents to the individual sensor 402/403 reservoirs 404 (via the internal distribution channels 407 contained within the catheter 400 infrastructure). At the time of targeted drug delivery, an available option is to engage dilatable balloons from each end of the catheter 400, thereby providing stasis of flow and allowing the delivered drug to remain in a relatively fixed sensor 402, 403 location (i.e., specific area of interest).

The ability to have multiple reservoirs 404/405 within an individual device 400/401 provides for storage and distribution of multiple different drugs or chemical compounds used for different pathologies (i.e., infection, thrombolysis, chemotherapy), where the ability to deliver multiple pharmacologic agents at a given time includes examples where an infected thrombus requires both thrombolytic and antibiotic drug therapy. Thus, this external method of drug delivery provides an effective method of delivering the specific pharmacologic agent which is required for the clinical situation encountered.

The concept of using a secondary medical device in concert with the primary medical device (for transportation purposes) can also be applied to diagnosis. While biosensors have a number of unique diagnostic functions, there may be situations where the diagnostic functionality or accuracy of the embedded biosensor cannot provide accurate diagnosis. In this situation, the specimen obtained by the primary medical device (through the use of microneedles for aspiration or biopsy) can be transferred to the secondary medical device (in essence reversing the transfer process previously described for pharmaceutical delivery), where it is stored and subsequently transferred for in depth genetic, chemical, histologic, and/or pathologic analysis.

To illustrate, in FIG. 5, a medical device 500 directed biopsy or aspiration is performed, where the focal area of interest is aligned with an individual biosensor 502 (or group of biosensors). In this process, the abnormal tissue or cellularity is detected through the release of chemical compounds (e.g., prostaglandins, cytokines) or DNA sampling. Before the actual biopsy apparatus 501 is activated, a data verification step may be required to ensure that the original analysis of the presence of local pathology is confirmed. Once confirmed, the biopsy process is activated, with the corresponding needle(s) (retractable needles for tissue biopsy and/or fluid aspiration) from associated biosensors 501 being released into the pathologic region of interest and suction is applied (via the corresponding pump apparatus (not shown)) to transfer the pathology specimen to the corresponding sensor reservoir 503 for temporary storage.

In a manner analogous to drug delivery transfer from the reservoir of one device to the reservoir of another device (as described in FIG. 4), a similar process can be used to transfer the pathology specimen from the reservoir 503 of the original medical device to the storage reservoir 504 of a second receiving device 501, which is then externally retrieved via needle 507 connected to pump 508, for example, and emptied (into storage 509, for example). Of course, biopsy needle 507 could directly obtain a biopsy sample from an area of pathology interest (based upon biosensor data), and transfer the specimen to storage reservoir 504 or to reservoir 509 for later retrieval for pathologic analysis. The above provides for more elaborate testing of the biopsy/aspiration specimen.

After pathologic diagnosis is fully established, the same device and biosensors can be used for therapeutic intervention, which can take a variety of forms (e.g. drug delivery, radiation, thermal ablation).

A relevant example may include an esophageal stent used in the treatment of esophageal cancer for the purpose of maintaining esophageal patency. If sensors in the stent wall identify the presence of cellular debris which pose a risk of impending occlusion as analyzed by the program, it is important to differentiate between malignancy, infection, hemorrhage, and fibrosis—each of which poses a different level of concern and has a different form of treatment. If the esophageal stent is not equipped with the necessary sensor technology for accurate diagnosis but does have the ability to perform biopsy/aspiration at the specific location of concern, then the biopsy/aspirate can be transferred to a secondary medical device 501 for subsequent in depth analysis. Suppose in this example the specimen is determined to represent malignancy (through DNA analysis and cytology analysis by the program). The secondary device 501 can in turn be used to deliver the chemotherapeutic agent of choice for local delivery at the specific sensor location in which the abnormality was detected.

In addition to drug delivery, a number of other therapeutic options may be available and integrated into the medical device sensor technology including (but not limited to) thermal ablation, cryotherapy, radiation, radiofrequency pulse therapy, hormone therapy, immunotherapy, and even surgery. In addition to cancer, other forms of pathology may benefit from medical device intervention. One example is the thrombus and debris which often forms in different vascular devices including stents, catheters, and filters.

An alternative treatment option for thrombus (in lieu of pharmacologic therapy) may include thermal ablation to "melt" the thrombus or debris when it exists in large quantity and may be difficult to treat with drug therapy alone. This may be the case with intravenous and intra-arterial filter devices, whose primary purpose is to trap debris and thrombus to avoid distal migration and life threatening complications (e.g., stroke, myocardial infarction, pulmonary embolus). As thrombus accumulates within these filters, the volume burden may become so extensive it may impair function of the filter. This is especially the case in acute events where large showers of debris are released by an inciting event (e.g., detached large deep venous thrombosis, interventional procedure such as angioplasty). In these situations the embedded sensors within the medical devices may perform both diagnostic and therapeutic functions. From a diagnostic standpoint, the sensors may not only detect the presence of thrombus/debris, but also quantify the volume, rate of accumulation, duration of active collection, and specific location within the device in which accumulation is greatest, using the program. As the debris/thrombus is detected at specific sensor locations, the therapeutic function may be locally deployed (e.g., thermal ablation, radiation), in an attempt to quickly and effectively eliminate the offending agent. By having the program continuously monitor disease progression and response to treatment, the treatment regimen may be modified in real time, in order to optimize therapy and minimize adverse effects (e.g., local tissue damage). This in essence, creates a "smart" medical device with diagnostic and therapeutic capabilities, with the ability to continuously monitor and modify therapeutic response in accordance with active data collection and analysis.

In addition to therapeutic intervention of disease, another important therapeutic application of the present invention is the ability to detect and respond to structural deficiencies in the medical devices. As previously described, sensors embedded within the walls of a medical device may be used to detect structural deficiencies or breakage of device components. The treatment for these device structural deficiencies can highly vary in accordance with the specific type, severity, and location of the abnormality; as well as the specific type of medical device.

In the example of an endoluminal stent graft in the abdominal aorta, leakage may be detected which, depending upon its severity, may be life threatening. Creating the ability to detect device structural abnormalities at early stages (through the capabilities of diagnostic sensors embedded within the device walls), presents an opportunity for intervention at an earlier point in time, which is currently not available. In the case of the leaking stent graft, a partial defect in the stent wall may be acted upon before it becomes a through and through complete wall defect. One option would be the local release of a biologically safe compound (e.g., epoxy or resin), which can seal the defect and strengthen the stent wall. An alternative strategy would be to use microsurgery techniques to effectively suture the wall at the site of defect. Both local drug delivery and surgical functions have been described with sensor technology and could become theoretically possible as intervention strategies for certain types of device structural deficiencies.

Figure 6:
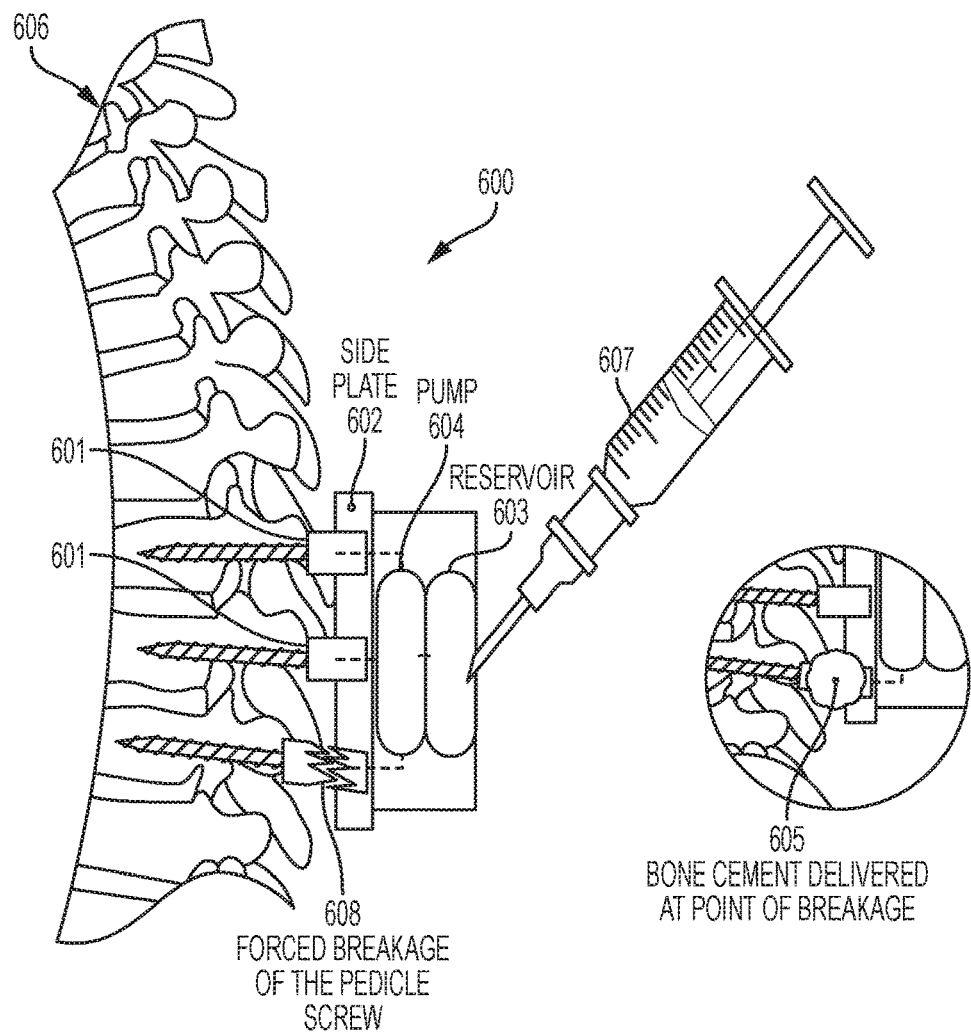
FIG. 6 is a schematic diagram showing a medical device system including a surgical device (e.g., spinal fixation hardware with side plate and pedicle screws) which is implanted for the treatment of underlying skeletal pathology, according to one embodiment consistent with the present invention.

Another example of a medical device prone to structural deficiency and leading to device failure and various medical complications are surgical fixation devices and prostheses. In the example of commonly used spinal fixation devices (e.g., pedicle screws—see FIG. 6, screw 601, for example), breakage frequently occurs, leading to device instability, pain, and abnormal motion. As shown in FIG. 6, a surgical device 600 (e.g., spinal fixation hardware with side plate 602 and pedicle screws 601) is implanted for the treatment of underlying skeletal pathology (i.e., lumbar spine spondylolisthesis). During the course of routing biosensor analysis (sensors (not shown) located within side plate 602), a breakdown in device integrity is detected, such as the breakage of a pedicle screw 608, which can lead to pain and instability.

Conventional strategies range from conservative management (for pain relief) to device removal. An alternative treatment option may include the local release of a mechanical stabilizer such as a biologic cement or polymers 605 (i.e., methyl methyacrylate or bone cement, for example) at the site of diminished device integrity (prior to outright breakage), which can serve to strengthen the device 600 and stabilize the underlying anatomy (e.g., spine 606). This can be accomplished by accessing the device reservoir 603 (which has been strategically located in a superficial location) under imaging guidance (e.g., CT, ultrasound), and introducing the chemical compound 605 into the device reservoir 603 through a percutaneous injection using a needle 607. Once received in the reservoir 603, the pumping mechanism 604 of the device 600 can be deployed, which provides energy to deliver the chemical/drug 605 to the specific location/sensor (within side plate 602 at the location of pedicle screw 608) of interest, where it is injected into the adjacent tissues (i.e., through a sensor deployed needle—in side plate 602, for example).

Since transport delivery of these substances would not be practical in a non-vascular location, this type of intervention would require local storage of the commonly used chemical compounds within the internal structure (i.e., at reservoir 603) of the device 600. Further, since these complications are fairly commonplace, statistical analysis by the program of the device database (specific to the anatomy, primary clinical condition, device used, and patient profile) can provide insight as to the most commonly encountered problems and most effective intervention strategy.

The ability to continuously collect and analyze targeted biosensor derived data provides a unique method of measuring the success or failure of the specific intervention strategy and determining the need for additional and/or different intervention. Using this data-driven knowledge, device manufacturers can incorporate this information into device design and storage options. Further, the program records all relevant data into the device database, which can be used for creation of customizable best practice guidelines, technology assessment and refinement, and clinical outcomes analysis.

In other devices, "refueling" via a vascular catheter, noted above for example, is not a viable option in surgical hardware (since it is routinely positioning outside of the bloodstream). Thus, an alternative strategy for drug delivery to the medical device is required. One method in which this can be accomplished is percutaneous injection into the centrally located storage reservoir (i.e., reservoir 504, for example) of the medical device. By strategically positioning the reservoir in the most superficial portion of the medical device and readily identifying it through a visual aid, a provider could inject the desired chemical or pharmaceutical directly into the storage reservoir through a syringe and needle. Once this drug delivery has been completed, the same system of distributed flow from the reservoir to the specific sensors of interest can be accomplished through a series of micropumps and microneedles contained within the biosensor delivery network. A variety of visual cues can be utilized for labeling of the medical device main storage reservoir such as radiopaque markers which are directly visualized by standard medical imaging techniques (e.g., CT, x-ray).

An alternative strategy would be to connect the central device storage reservoir with an injectable subcutaneous port, which can be readily accessed via a needle and syringe, in a manner analogous to conventional Mediport catheters. Regardless of the strategy employed, the end result is the same; the central storage reservoir of the medical device can be accessed through an external delivery system, from which it transports the corresponding agent to the specific sensors in direct proximity to the structural defect, where it is injected. Subsequent sensor derived data can assess the relative success or failure of the intervention and this data can in turn be recorded in the device database by the program, so as to track and analyze different intervention strategies for future applications.

Another type of non-drug delivery intervention which may prove to be frequently utilized is the ability to treat active bleeding at the medical device site. Since placement of these devices can often be traumatic in nature, it is not uncommon to experience localized bleeding, which if left untreated may result in serious complications. In addition to local pharmaceutical intervention (e.g. clotting agents), the sensors embedded in the device can deploy cauterization, in an attempt to mitigate bleeding. Since cauterization may result in local tissue damage (via thermal injury) it is essential that the intervention may targeted and narrowed to a small focus, which is highly achievable with embedded sensors which can localize the focal point of active bleeding.

Mobile Sensor Embedded Medical Devices

Figure 7:
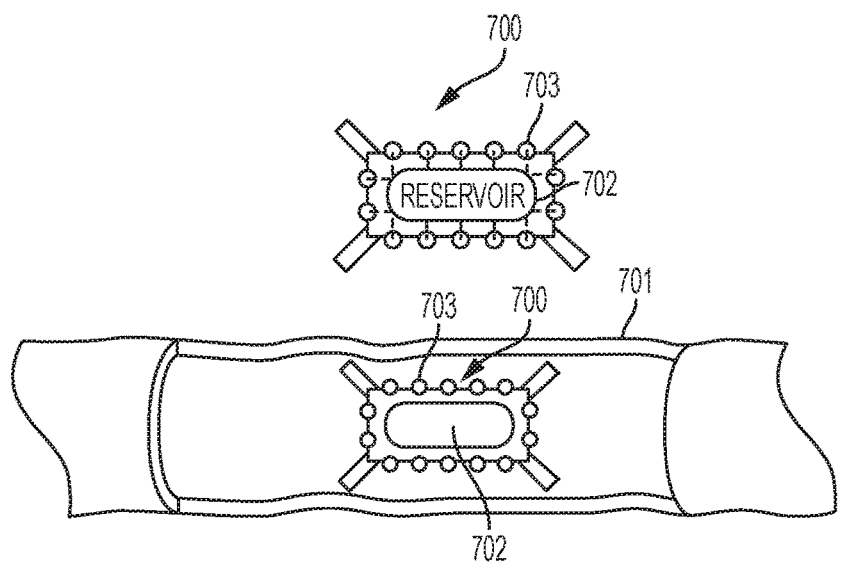
FIG. 7 is a schematic diagram showing sensor embedded mobile medical device, which can effectively travel throughout the human body, according to one embodiment consistent with the present invention.

Up to now the discussion has focused on stationary medical devices, which are relatively fixed or static in position. The very nature of their fixed anatomic positioning provides them with the ability to diagnose and treat local pathology only. An additional application of the invention is the creation of sensor embedded mobile medical devices 700 (see FIG. 7), which can effectively travel throughout the human body in their search for sites of pathology and potential intervention. Organ systems which accommodate this active transport include the blood stream (e.g., vein 701), cerebrospinal fluid, respiratory airways, gastrointestinal tract, and urinary system.

A number of existing and emerging technologies could be applied to this application including (but not limited to) ingestible pill cameras, smart pills with embedded chips, and nanobots (sometimes referred to as nanorobots). These non-traditional medical devices can contain embedded sensors and can be used for "mobile" diagnostic and therapeutic applications. Regardless of the specific technology employed, the concept includes a miniaturized device 700 containing embedded sensors 703 is placed within the organ system of choice, and can be a self-propelled fully functional medical device which has the ability to actively travel throughout an organ system and interact with local tissue or other medical devices. During the course of its navigation, it continuously obtains diagnostic data in the local milieu, which can be specific to a certain medical disease or condition or generalized in nature. The self-propelled migratory biosensor 700 can contain a high concentration of embedded diagnostic sensors customized specifically to the organ system to which it is deployed (e.g., bloodstream, cerebrospinal fluid, gastrointestinal tract, genitourinary tract), and may periodically obtain local cellular or fluid specimens.

As an example, if a patient is thought to have an infection or inflammatory process in their gastrointestinal tract (e.g., Crohn's disease, diverticulitis), the sensors 703 within the ingested biosensor 700 can sample local contents throughout the gastrointestinal tract for disease markers or chemical mediators and transmit the information wirelessly to be received by a detection device, which will record the data, including the specific location of abnormal data. While a variety of methods can be used to record location when local pathology is detected, the specific anatomic region of concern can be localized (i.e., marked) by deploying a biological marker (e.g., diode, radio transmitter), or labeled biodegradable suture which can be deployed in the bowel wall, for example, at the location of interest, which can server for future localization and intervention. The labeling of the labeled biodegradable suture could include a radioactive tag, fluorescent marker, or light emitting diode.

Generally speaking, the mobile sensor 700 actively records data while in transit throughout the body, and marks the location of pathology which specifically maps to a data point of interest. If multiple areas of abnormal data are identified by the program, each designated location can be differentiated from its counterpart by a unique identifier by the program in the labeling process. This provides the ability to record and differentiate multiple data abnormalities and anatomic locations within a single organ system.

At the time each data element is recorded and its corresponding anatomic location marked by the program, a date and time stamped entry is recorded by the program in the medical device and patient specific database. This provides a cumulative record of sequential data over time, along with the corresponding anatomic location, which can provide insight as to disease progression or improvement. This longitudinal data can in turn be used by the program to create a 4-dimensional time activity curve which shows changes in data measurements over time specific to a focal or regional anatomic location.

In the example of a patient with Crohn's disease, sequential data collections may show inflammatory markers over multiple segments of the gastrointestinal tract, each of which deviates in its degree of inflammatory change over time. The resulting 4-dimensional data map created by the program, graphically displays which anatomic regions demonstrate the highest levels of inflammation, temporal change over time, and new emerging areas of inflammation. Continuous data collection provides an in vivo method of measuring disease progression as well as response to treatment. In a similar manner, nanobots 600 can be placed in the bloodstream, airways, urinary tract, or cerebrospinal fluid to perform similar functions.

Similar to the case of stationary medical devices, these mobile medical devices 700 with embedded sensors 703 can also be used for therapeutic purposes, along with diagnosis. Suppose for example, a nanobot injected in the bloodstream identified an active site of arterial bleeding in the liver following trauma or of venous varices in the setting of cirrhosis (e.g., through miniaturized cameras). The nanobot 700 could mark the site of bleeding with a biological marker, which can be subsequently used to guide therapy by a secondary medical device with capabilities for drug delivery (e.g., vasoconstrictive agents). The therapeutic device would guide itself to the specific bleeding site through tracking of the marker and once found and bleeding confirmed (through embedded sensors and/or cameras), deliver the therapeutic agent in a manner similar to that described above with stationary medical device therapy. While the mobile diagnostic medical device could in theory also serve as a source of intervention, this would be problematic to date given the size constraints of the reservoir 702 contained within it.

Further, within the near future, mobile medical devices 700 with embedded sensors 703 could also be used to perform DNA analysis at the cellular level, in the hope of in situ cancer detection. Once identified, these very early cancers can undergo treatment in a similar manner through the use of targeted intervention (e.g. immunotherapy, chemotherapy, radiation); delivered by miniaturized medical devices 700.

Database Analyses

The components and functionality of a medical device database similar to that of the present invention, have been described in U.S. patent application Ser. No. 15/257,208, filed Sep. 6, 2016, on "System and Method for Medical Device Security, Data Tracking, and Outcomes Analysis", which is herein incorporated by reference. The collection of standardized medical device data is used by the program to create a referenceable database, which provides a user with the ability to comingle data from a large number of healthcare institutional and individual providers, patient populations, and technology providers. The resulting large sample size statistics provide a bevy of data-driven (i.e., evidence based) analytics along with objective clinical decision support tools and best practice guidelines.

The medical device analytics derived by the program from these medical device databases can be customized in accordance with the individual patient, technology in use, healthcare provider (at both individual and institutional levels), and clinical context (e.g., primary disease, comorbidities). This ability to personalize medical device data and derived analytics is facilitated by the creation of a standardized profile system which takes into account individual attributes and historical data specific to patient, technology, provider, and clinical disease and utilizes the resulting profile schema to customize the analytics in association with "similar" reference groups.

There are four individual categories of analytics which can be derived by the program from the medical device database and these include Risk, Predictive, Diagnostic, and Therapeutic analytics. Risk analytics utilizes data specific to the individual patient, technology, provider, and disease process to perform a risk analysis in accordance with historical medical device data. As an example, a patient who is undergoing spinal fixation for a grade 2 spondylolisthesis at the L5-S1 level can undergo statistical analysis by the program of the medical database to determine the relative risk of developing certain post-procedural complications (e.g., spine instability, infection, device breakage) based upon historical analysis of the surgeon performing the procedure, specific surgical device being used, and patients with similar characteristics as defined, for example, by the Components of the Patient Profile:

1. Physical Attributes
2. Genetics
3. Intellect
4. Lifestyle/Activity
5. Clinical Condition and Comorbidities
6. Compliance
7. Communication
8. Occupation
9. Medical Technology Since each of these variables will have their own unique risks for developing individual complications, the derived Risk Analysis by the program is a dynamic calculation which is a composite of the multiple variables of interest. If, for example in the preoperative assessment, a higher than expected (i.e., relative to the baseline statistical analysis) risk for device breakage is determined by the program for the technology being used, an alternative risk can be calculated by the program, of replacing the planned device with a number of alternative technologies, with the goal of identifying the specific device which best fits the disease process being treated (i.e., grade 2 L5-S1 spondylolisthesis) and patient attributes (e.g., 300 pound 66 year old sedentary female with underling diabetes). In this risk analysis, a comparable device may prove to have a lower statistical risk for the given patient and disease, and as a result the surgeon may elect to substitute the originally planned technology with that of the preferred technology (based upon statistical analysis by the program of the medical device database). This information may also prove to be of value in acquiring approval from the designated third party payer, who may be reluctant to agree to pay for the more expensive surgical device in the absence of objective data and patient population statistics. A similar analysis may prove to be useful to the patient in selecting the surgeon of choice, based upon their historical post-procedural complication record as it relates to the disease, patient profile, and technology being used.

The next class of analytics which can be derived by the program from the medical device database are Predictive Analytics, which attempts to use historical data of similar profile groups in combination with prospective medical device data to predict outcomes and risk of complication (before it becomes clinically observable). In this situation the aforementioned Risk analysis is combined by the program with ongoing data being collected in real time from the medical device sensors to provide an up to date prediction of future complication risk. Since the prospective data being collection represents a continuum in the overall spectrum of disease and treatment, the earliest data deviation from the patient's baseline may be too small to accurately determine the presence of a device structural complication (e.g., breakage) or medical disease (e.g., infection). After all, small fluctuations in data measures would be expected under normal conditions and many of these small data variations prove to be inconsequential. If however, these small data variances are combined with statistical risk analysis, one may be able to more accurately differentiate early pathology from that of normal variation. This combination of risk and subtle deviation in real-time device data constitute Predictive Analytics. The ability by the program to use patient and technology specific historical risk and sensor derived objective measurements with outcomes data contained within the device database, may provide even greater predictive accuracy as to the presence or absence of early pathology.

Suppose in the prior example of the grade 2 L5-S1 spondylolisthesis, the risk relative to the patent, technology in use, and surgical provider were all found by the program to be lower than normal. In the event that sensor derived data began to show small variation in device position, the Predictive Analytics remain relatively low so no change in management is deemed necessary or recommended by the program, other than a slight increase in routine surveillance measurements. On the other hand, if the abnormal sensor measures were restricted to a single device location (e.g., at the interface of the L5 pedicle screw 501 and surgical side plate 502), the focality of the data variation found by the program, may prove to be of greater risk for an early structural deficiency in the device. When this same data is cross referenced by the program with outcomes analysis of the device database (taking into account the specific device location, degree of data variation, technology in use, and patient profile), a more refined Predictive Analysis measure can be calculated by the program.

In the next type of analytics (Diagnostic Analytics), the sensor derived real time measures are the primary source of data used by the program for the detection of pathology. As previously mentioned, small variations from baseline are relatively common and represent the normal and expected two standard deviations, which define the "normal limits" of data. Once data is consistently recorded and validated by the program that exceeds these normal limits, then pathology becomes of high concern. The ability to continuously record serial data measures provides important validation in the detection of true pathology, while also allowing the program to assess the clinical severity of the problem (by measures of magnitude and temporal change in data measurements). At the same time, correlation of medical data by the program (e.g., laboratory, physical exam, clinical testing) may often prove to be of value in substantiating the abnormal biosensor data and confirming the pathology in question. The trending analysis derived by the program, of biosensor measures (and correlating clinical data), can in turn be cross referenced by the program with the comprehensive medical device database (which contains historical outcome data), to provide increased sensitivity and specificity as it relates to specific disease and patient/technology profiles. The ultimate goal of these Diagnostic Analytics is to accurately detect the presence of early disease, characterize the specific disease in question, provide correlation with other clinical data measures, and guide intervention with the goal of optimizing clinical outcomes.

The final class of analytics derived from the medical device database is Therapeutic Analytics, which provides information related to intervention options (for the abnormal data in question) relating to the specific technology in use, patient profile, and clinical disease (and comorbidities). The ability of the program to use historical data from the medical database to determine intervention strategies is an integral component of Therapeutic Analytics, for it provides insight as to how previously attempted interventions affected clinical outcomes. In addition, the ability of the program to provide continuous real-time sensor derived data before and after interventions serves as an important method for measuring the clinical effectiveness of the intervention strategy employed. In the previously cited example of the grade 2 spondylolisthesis with early signs of device breakage, the most important decision to be made (once the diagnosis of breakage is confirmed), is whether conservative management or device replacement is required. Having the ability to customize (or personalize) the decision making process is possible by the program retrospectively analyzing medical device data and intervention strategies of similar patients and technologies. If for example conservative management (e.g., physical therapy, modification of physical activity, muscle strengthening exercises) was found to be beneficial in a certain subset of comparable patients and technologies, then more detailed analyses by the program of these cases may prove to be beneficial in optimizing strategy and customizing it to the specific attributes of the patient. Lastly, the program also has the potential to identify limitations in existing intervention strategies and serve as a tool for analyzing new medical treatments and technology refinements. In the case of device related infection, as new antibiotics and treatment regimens are employed, the program can correlate clinical disease and treatment response as it relates to specific technologies and patient profiles; so as to provide clinical decision support specific to the individual patient and device.

Communication and Data Networks

The components and functionality of a medical device database similar to that of the present invention, have been described in U.S. Provisional Patent Application No. 62/295,787 from which this application claims priority, and which is herein incorporated by reference. The data network of the present invention (see FIG. 8) includes the following components:

1. Primary medical device (and embedded biosensors) 801.
2. Local storage device 802 (e.g., smart phone).
3. Centralized CPU (microprocessor) 803 of local storage device 802 or client computer 812.
4. Centralized Storage device (memory) 804 with program 808, and external storage 809 if required.
5. Other medical devices 805.
6. Other medical databases (e.g., electronic patient record, etc.) 806, or other regional databases.
7. Internet 807.
8. Display 810 and input means 811 for the client computer 812 or local storage device 802.

The CPU 803 of the client computer 812 (and/or local storage device 802) is effectively the "brain" of the operation. All data passes to and from the CPU 803 (i.e., multidirectional data flow), where it undergoes analysis by the program 808, which creates a series of analytics which are storied in the centralized database 804. Note that this centralized database 804 can be remotely located (e.g., database 809, cloud-based) or locally situated (e.g., hospital based) and exist in multiple versions for the purpose of redundancy.

The primary data which is produced by the medical device 801 and its embedded biosensors is first transmitted to a local storage device 802. While this could potentially be located within the device 802 itself, physical size constraints within the device 802 may make this option impractical. The local storage device 802 may exist in a number of forms (e.g., smart phone, smart watch, wearable computer) and functions to receive and store data via wireless transmission as it is produced in the medical device 801. A number of known wireless transmission options exist in standard telecommunications.

The local storage device 802 would store the raw data obtained by the medical device 801 in memory 804, and upon receipt, transmit a signal back to the medical device 801 confirming successful data transmission. Once the raw data is received and stored in memory 804 in the local device 802, it may or may not undergo some degree of data processing using a CPU 803, depending on the type of data. While complicated data processing and analysis is largely confined to the CPU 803 of a client computer 812, the local device 802 may be equipped to handle processing of small data components, specifically related to emergency or stat data measurements. In this situation, processed data can be simultaneously sent from the local device 802 to the patient, provider, CPU 803 of the client computer 812, and central database 804, 809.

Since the local storage device 802 is relatively limited in storage apace and functionality, the data it receives from the medical device 801 is subsequently transmitted to the CPU 803 of a client computer 812 and central storage 804, 809. The majority of data processing and analyses are performed by the program 808 at the level of the client computer 812. Once completed, these analytics can be sent by the program 808 to a number of authorized sites in the network including (but not limited to) the patient, provider, local storage devices 802, medical device 801 (and its embedded sensors), and other medical databases 806 (e.g., electronic patient record). In addition, a MESH network allows direct connection between multiple medical devices 801 within the patient.

Since a large number of individual sensors may be contained within a single medical device 801, it is important to ensure that each individual sensor's data is accurately compartmentalized and accounted for. In order to do so, the following data from each individual sensor is included in the recorded data: sensor type, functionality, physical location (within the medical device), date/time of recorded data, and specific data measurement. In turn, bidirectional data flow from the CPU 803 to the individual sensor can direct modification in individual sensor activity. From the diagnostic perspective, these sensor actions include the specific type, duration, and timing of data collection.

Alternatively, sensor actions can be therapeutic or interventional in nature (e.g., biopsy, drug release), and the direction of corresponding sensor actions are driven by CPU 803 driven data transmissions. Some sensors may have the ability to perform both diagnostic and therapeutic functions as noted above; the actions of which can be controlled through data directives from the CPU 803 (via the clinical provider). The fundamental ability for multidirectional flow of data between the various components within the data/communication network provides the capability of continuously modifying medical device 801 (and individual sensor) function and data collection.

In addition to medical device derived data, many other data sources exist within the network which are fundamental to medical device function, clinical diagnosis, and therapy. These alternative data sources include (but are not limited to) the patient, clinical providers, technology producers, and a variety of non-device medical databases. If for example, a patient wants to record physical activity or symptoms at a specific point in time (e.g., which may correspond to simultaneous sensor data collection), he/she can input the data (via text or speech) to the local storage device 802, which in turn transmits it to the CPU 803 and central database 804 of a client computer 812.

Alternatively, if the physician provider after receiving data analyses on recent sensor data from the client computer 812, wishes to modify sensor activity (e.g., frequency with which data is collected), he/she can input a directive from their client computer 812 to the device client computer 812 and its CPU 803 for processing. In many instances, ancillary clinical data contained within the patient electronic medical record (from database 803) is directly applicable to medical device data. Using artificial intelligence (e.g., neural networks) or rules based techniques, multidirectional queries and data sharing may be performed between the client computer 812, long term device data storage 804, 809, and the medical database 806, to facilitate improved knowledge and diagnosis.

Lastly, a technology vendor may wish to introduce a software upgrade to the medical device 801, which can be accomplished remotely through electronic transmission over the Internet 807 to the medical device 801 CPU 803. Once this data is authenticated and validated by the program 808, it can in turn be transmitted to the medical device 801.

Even interpersonal communications related to the medical device 801 can be recorded, transmitted, received, and analyzed through the medical device network. If for example, a patient wishes to share information or a question regarding the medical device 801 with their clinical provider, they can do so by recording the information in their local device 801, which in turn transmits the data to the local storage device 802 and/or client computer CPU 803, where it is processed by the program 808, and subsequently transmitted to the local device 801 of the physician. The data transmitted from the local storage device 802 or client computer 812 to its intended recipient is also copied and stored by the program 808 in the long term database 804, 809 for future review as needed. The ultimate goal is to create a medical device network which facilitates rapid, accurate, and comprehensive data collection, transmission, and analyses between multiple data sources including individual biosensors, medical devices, databases, and personnel.

Quality Assurance, Quality Control, and System Security

One of the most important aspects of the invention is creating the ability to routinely monitor and assess performance quality, as it relates to technology performance (of the collective and individual components within the medical device), data accuracy and consistency (as it relates to the sensor derived data and database analytics), appropriate usage by authorized end users (including patients, clinical providers, administrators), and communication (relating to the individual components of the network and participants). Ongoing quality assurance (QA) and quality control (QC) is critical in ensuring that clinical outcomes are optimized and the various technology components and involved persons are accountable in a reproducible and standardized fashion. The resulting QA and QC data are in turn also recorded by the program in the medical device database and subjected to prospective analysis in order to assure uninterrupted and continuous quality performance.

Assessment of diagnostic sensor performance involves the routine monitoring of data collection and verification by the program. In the event that a scheduled data event is not successfully recorded in the database by the program, then an automated data audit is performed by the program to identify the specific site (within the overall network) of data loss. Since this could occur at the level of the biosensor, local storage device (e.g., smart phone), or central storage device, a data retrieval inquiry is sent by the program to all technologies specific to the time of the scheduled data event to identify the specific location in which data failure occurred.

If the biosensor is determined to be the offending component by the program, and subsequent scheduled data events are also interrupted, then that specific biosensor is removed from ongoing data collection and analysis. In the event that multiple biosensors become deficient to the point that ongoing data collection and analysis is compromised as determined by the program, then device removal and/or replacement may be recommended. Technical deficiencies in the local storage device or other devices or computers are far easier to address since they are external to the patient and directly accessible to maintenance. In the situation where the medical device is externally located (e.g., cutaneous device), then sensor repair and/or replacement is a more viable option. The resulting QC testing data is stored within the central device database by the program, and also used for prospective analysis since it can serve as a valuable resource in identifying and characterized technology breakdown. As new or refined biosensors are introduced in various medical devices, this program analysis is critical in objectively analyzing comparative technology performance.

In addition to "internal" quality assurance methods, an alternative QA strategy includes creating and using "external" technologies for medical device/sensor QC and QA. This "external" strategy would include a variety of devices which could externally assess sensor/device operation, functionality, integrity, and discriminatory capabilities. Two primary classes of external QA/QC devices include those that are operated manually and those that operate independently. A manually operated device would be controlled by a third party, which would direct its navigation, device-device interactions (and communications), and testing protocols. Examples of manually operated QA/QC devices may include (but are not limited to) steerable catheters, nanobots, and capsules. Like the medical devices they are testing, these devices would have self-contained sensors, reservoirs, and injectors which could effectively store and release a variety of known chemical compounds which upon release be used to determine sensor detection within the medical device being tested. In addition, the release of these chemical compounds (of known identity, dosage, and concentration) can be used to assist in medical device calibration, which is an integral component of QC. After release of the known chemical by the QA/QC test device, the response of the individual medical device sensors can be reviewed and analyzed to determine accuracy in identification and quantification of the chemical compound in question.

Based upon this test data of individual sensors, individual and collective sensor calibration within the primary medical device can be performed through wireless communication of individual sensor software upgrades. After these calibration upgrades have been successfully uploaded, a repeat test dose can be delivered by the QA/QC device for the purpose of repeat post-calibration analysis. In the event that individual sensors remain suboptimally calibrated, two options can be employed. If the calibration error is relatively minor, the involved individual sensor can have its data mathematically corrected based upon calibration analysis. Alternatively, if the individual sensor's calibration analysis exceeds a pre-defined QA threshold, then it is effectively "turned off" for future real-time data collection and analysis.

In the case of multifunctional sensors, the QA response of each sensor may be dependent upon a specific action or compound being tested. In this scenario, each individual sensor function is independently analyzed for quality assurance. As an example, take the setting where an individual sensor may have capabilities of monitoring for the presence of three different chemical compounds. If QA testing reveals that two of these chemical compounds are accurately analyzed but one is not, then the sensor derived data for the two "intact" functions is actively maintained, while the sensor derived data from the function which is "faulty" is modified or turned off by the program. The net result is that external QA/QC testing provides an alternative method of continuously measuring sensor performance and derived data, while also providing a method of intervention for the purpose of optimizing sensor performance in the presence of inevitable day to day quality degradations.

The category of "independently" operated QA/QC devices includes devices which have the ability to travel and operate independent of manual control. As an example, a self-propelled nanobot could effectively enter the human body organ system of interest (e.g., bloodstream, gastrointestinal tract, genitourinary system) and be tasked with locating medical devices in vivo, and subsequently perform QA/QC testing. In order to identify the presence of such an in vivo medical device, embedded sensors within the device would have the ability to emit a "homing signal"; which may represent transmission of a frequency of sound or light after receiving an authentication prompt from an external source. This authentication prompt would include a predetermined signal specific to each individual medical device based upon the registration data of each individual device (which was described in U.S. patent application Ser. No. 15/257,208). In the absence of successful device authentication, the device specific homing signal would not be activated by the program, which would make device localization and device-device synchronization difficult (if not impossible). This represents an added security feature of the invention, in order to prevent unauthorized device-device interactions.

Once the QA/QC device recognizes the homing signal of the in vivo device to be tested, it can travel to the specific location (or in close proximity) in which the device resides and undergo a synchronization process (which is similar to that described above in the section of device-device drug transport). This allows for the QA/QC testing device sensors to be directly aligned with the individual sensors within the in vivo device, which allows individual sensor QA/QC testing and analysis. As the specific quality test is performed (e.g., release of specific chemical compound), at a known physical location, analysis by the program of the in vivo medical device sensor-derived data can determine individual sensor functionality. Since these QA/QC testing devices have the ability to perform multiple functions and store multiple chemical compounds (via individual storage reservoirs), these devices can perform a myriad of quality testing at a single point in time.

In addition to program analysis of chemical testing, these devices can also perform analysis of the physical integrity of the medical device through ultrasound. The ability to synchronize the physical locations of the testing and in vivo devices provides an accurate method for creating a "physical integrity map" of the medical device. If transmitted and received ultrasound signals reveal a structural defect in the device, the specific location of this defect can be identified and undergo repeat (and more in depth) testing over time, thereby creating a longitudinal map of medical device physical integrity (and sensor function) over time. If the location of involvement becomes severe enough to impair device function and/or patient safety, then one of two options can be employed. The first option includes device removal, while the second option includes device repair. In this scenario, the QA/QC testing device can be modified to create surgical functionality, which can be manually controlled to perform "surgery" on the device in the region of impaired integrity, in an attempt to prolong the lifetime and functionality of the impaired device.

Regardless of the quality test and analysis being performed, the recording, tracking, and analysis of sensor derived data by the program, are important aspects of the present invention, and an integral component of the device database. Data accuracy and consistency has been mentioned earlier and it is an important concept since it helps providers determine the reliability and clinical importance of recorded data outliers. The ability of the program to continuously track and analyze synchronous and sequential data measurements with neighboring sensors provides a user with the ability to differentiate between pathology related and artifact related data abnormalities. In the event that an abnormal sensor derived data measurement is not substantiated by comparable measurements in the neighboring sensors, or repeat measurements within the same sensor, then one can assume the recorded measure was spurious and the program can automatically provide the system administrator with an automated prompt or alert for more in depth sensor QC testing.

Analysis of device and database usage by various personnel (e.g., patients, clinical providers, IT and healthcare administrators, researchers, payers, technology producers) is a critical component of the QA program. In current healthcare practice, data privacy and security concerns are of the utmost importance and cannot assume to be adequately addressed without continuous monitoring and scrutiny. Since access to the medical device and associated database requires a formal registration process (which was described in detail in U.S. patent application Ser. No. 15/257,208) before being granted authorization privileges, the unique identifying data for all end users is well established before one can record, access, query, or communicate with the medical device database or other authorized end users. The corresponding unique identifying data is designed to include a variety of data elements including (but not limited to) biometrics, alpha numeric, textual information, speech, and facial recognition. In order to improve security features for anyone seeking access to the system, a randomized computer generated authorization query is submitted each time an individual seeks to access the database.

An additional security feature incorporated into the invention is the creation of a tiered prioritization schema which effectively places data and requested authorization privileges into three categories (e.g., low, medium, high), in accordance with clinical importance and sensitivity of the involved data or requested actions. Examples of these different data/action tiers include the following:

Low Security Data/Actions:
1. Input of subjective data (e.g., patient input of pain)
2. Retrieval of single biosensor diagnostic data measurement
3. Retrieval of routinely scheduled QA/QC analytics
4. Notification reminder of scheduled test/procedure
Medium Security Data/Actions:
1. Retrieval of weekly biosensor diagnostic data analytics (single device)
2. Communication between authorized end users (e.g., patient and physician)
3. Analysis of "before and after" biosensor diagnostic data (i.e., related to a therapeutic intervention)
4. Comparative analysis of technology performance (e.g., comparison of different manufacturer biosensor QA analytics)
High Security Data/Actions:
1. Biosensor drug release
2. Change in biosensor activity regimen (e.g., frequency/type of data retrieval)
3. Data communication between medical devices
4. Retrieval of biosensor data from multiple devices
5. Change in end-user authorization privileges or notification schema In a similar manner, individual devices can have different levels of assigned security in accordance with their functionality and clinical importance. As an example, a peripherally located intravenous catheter (used for venous access) may have a low security level, a coronary artery stent may have a medium security level, and a cardiac pacemaker may have an assigned high security level.

The methods and complexity of end-user authentication can directly reflect the three different levels of data and/or device security. Low levels of security would have a single step and user authorization process, which include a single authorization requirement (e.g., password entry). Medium level security would have a more intense authentication process which may include a two-step single user authorization process (e.g., biometrics, password). A high security request may have a three-step authorization process involving multiple end users; thereby ensuring that a single end user cannot proceed with a high security action or data request without confirmation from a second authorized individual. In the event that the second authorization party is not readily accessible, a predefined escalation pathway (notification via electronic means) would define an alternative end user option for authorization. If at any point in time, the authorization/authentication process is invalid or declined by security protocols, an automated alert is sent by the program to the database notifying of a potential security breach which mandates follow up action in accordance with the level of the security measure. In the event that the security breach is confirmed, all ongoing diagnostic and/or therapeutic actions are temporarily ceased pending a complete investigation.

Communication of the network components and/or authorized end users is another important feature of the QA, QC, and security programs. Since prospective data analysis requires continuous and uninterrupted flow of data from the medical device to the local storage device and subsequently to the central database, any interruption in data transmission will result in diminished functionality of the technology and increase the potential for adverse clinical events. The multi-directional flow of data between the network components can be routinely monitored and tested to ensure proper functioning. This communication testing should also include ancillary medical databases (e.g., electronic medical record, pharmacy information system). Similar routine testing of communication between authorized end users is another important component of quality testing, which includes periodic auditing of communication entries in the device database along with random communication tests.

Communications can also occur between different medical devices, which provides expanded ability to improve device diagnostic and interventional capabilities. As an example, if data output from sensors in a femoral venous catheter in a critical care patient with a bleeding ulcer, detects the early presence of thrombus (i.e., clot) formation adherent to the catheter walls, as analyzed by the program, the program would implement therapeutic action in the form of a local release of thrombolytic medication. At the same, the data from this central venous catheter may be communicated by the program to other devices (i.e., a Swan Ganz catheter in the pulmonary artery and endotracheal tube) as well as the patient electronic medical record in another medical database. These other devices may be "prompted" by the program to the development of thrombus in the catheter device, which may be programmed to increase their own diagnostic assessment for local thrombus or pulmonary emboli (which represents distal passage of the thrombus into the pulmonary arteries where it becomes trapped and can cause respiratory distress, diminished oxygenation, or even death). In response to this data from the femoral venous catheter, the program which operates the Swan Ganz catheter may institute an increase in data collection for a potential rise in pulmonary arterial pressure (caused by pulmonary emboli), along with increased detection of local thrombus in proximity to the catheter. At the same time, pressure and volume sensors within the endotracheal tube may increase their diagnostic regimen to identify early signs of increased airway resistance/pressure in association with pulmonary emboli.

In essence this represents a systematic response of multiple medical devices to diagnostic data from a disparate medical device, for enhanced diagnosis and treatment. At the same time, the data obtained from the femoral venous catheter causes the program to trigger an alert to the electronic medical record (EMR) for associated data of clinical interest (e.g., arterial blood gas measures, blood pressure). In the event that correlating data from the EMR is not readily available, an automated decision support prompt may be sent by the program to the clinical provider recommending the ordering of this additional medical data for enhanced diagnosis.

Thus, with respect to the above example, conventional medical therapy for a deep venous thrombosis includes systemic therapy (e.g., heparin), which would be contraindicated in this patient due to the presence of a bleeding ulcer. The ability for early detection and exact localization of thrombus is further enhanced by the ability to deliver therapy locally, without the use of systemic drug delivery which would be contraindicated by the presence of the underlying ulcer. This ability to communicate and analyze data from multiple devices, strategically extract relevant data from external medical databases, and intervene at a local level provides enhanced diagnostic and therapeutic opportunities.

Perhaps the best way to describe the functionality of the present invention and its use is to provide a few relevant examples, which can incorporate a number of different types of medical devices, clinical/technical scenarios, and patient variabilities. In the Figures, a few exemplary drawings are provided which illustrate how biosensors may be embedded in different types of medical devices for diagnostic purposes, and how corresponding therapeutics applications can be created.

In one example, a patient is planning to have a decompression lumbar laminectomy and fixation procedure for the treatment of multilevel spinal stenosis. Prior to surgery, the surgeon may elect to access the medical device database and its analytics, to determine the optimal technology to be deployed based upon the clinical condition being treated and specific patient attributes (i.e., Patient Profile). This decision support feature of the program provides statistical data based upon historical clinical outcomes data from a large sample of patients who have had medical devices deployed. The input data requirements for performing this technology analysis include the following:

1. Clinical provider name or Provider Profile Identifying Data
2. Patient name or Patient Provider Identifying Data
3. Clinical condition requiring medical device deployment
4. Location of proposed procedure (e.g., healthcare institution)
5. Technology preferences or restrictions Note: Any requested analysis or data entry into the medical device database first requires registration of the clinical provider, patient, institutional provider, and technology being used. The resulting input data is used to create the corresponding Patient, Provider, and Technology Profiles. When any of these pre-existing profiles are being accessed from the medical device database, a mandatory field for profile updates is required by the program to assure that the profile information used is accurate and up to date.

Once the requested technology assessment query has been completed, the authorized clinical provider will be provided by the program with a list of available technologies which satisfy the search criteria. The list of these technologies will be presented to the user by the program, in hierarchical order based upon analysis of technology adverse events, clinical outcomes, and economics. Corresponding data measures for each category of data are available by the program to the user to assist in the decision-making process, which can be individually accessed for more granular data. Once this analysis has been completed by the program, the clinical provider may use the data for technology selection. In the event that preauthorization is required by the payer, this data and resulting analyses by the program can be used to assist in technology comparative assessment and economic justification.

In addition to the selection of the individual type of medical device to be used for the planned procedure, technology specific diagnostic/treatment options can be reviewed and analyzed by the user and/or the program. This may entail presentation by the program, of different device options including (but not limited to) embedded biosensors which may serve both diagnostic and therapeutic purposes. The design, number, functionality, and distribution of these biosensors are in large part based upon the documentation and frequency of technical and medical complications related to the medical device and underlying clinical status of the patient. Patients, clinical conditions, and/or medical devices with higher rates of complications may have greater number of sensor deployment options; which ultimately factor in device selection.

The final medical device selection (including the specific type of device and its embedded sensor arrays) is presented by the program to the clinical provider prior to final approval with corresponding medical device data related to cost, historical complication rate, most frequent types of complication, therapeutic options incorporated in the device, and its expected lifetime. In the event that specialized sensor requirements are requested by the provider, a customized medical device may be required, which may require additional approval from both the technology provider and third party payer.

During the informed consent process (which is mandated and requires explanation of the procedure, potential complications, clinical risk/benefit analysis, and alternative treatment options), the medical device data and derived analytics by the program may be used to assist in patient education and decision making. During this process the selection of medical device technology will be discussed with the patient along with alterative treatment and medical device options. Associated economic data may also be included in this process in the event that additional and/or out of pocket expenses are to be incurred by the patient.

During the course of the procedure, a formal registration of the medical device (and provider) takes place which has been described in detail in the U.S. patent application Ser. No. 15/257,208.

Figure 9:
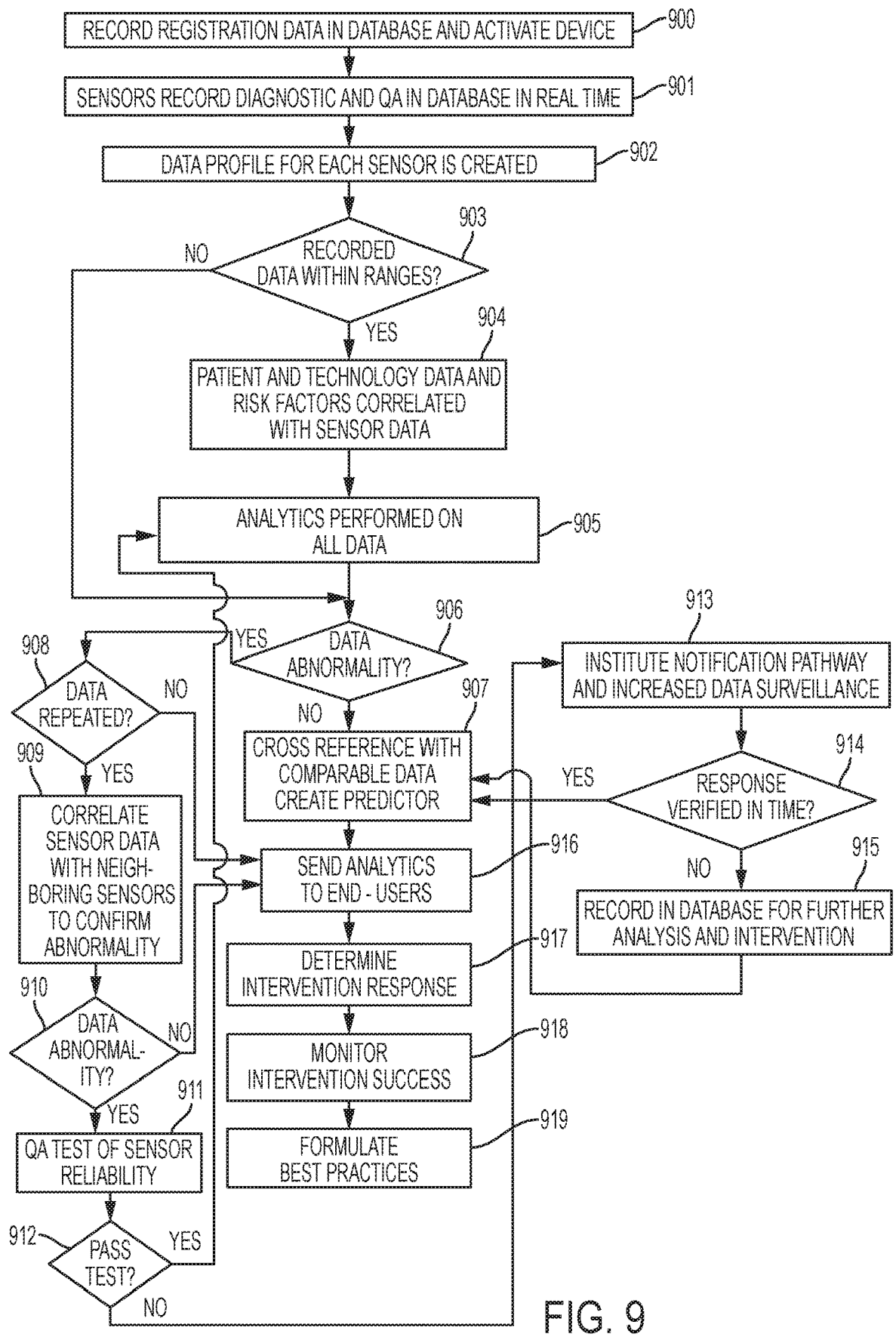
FIG. 9 is flow chart which show the major steps involved in accomplishing the methods of the present invention, according to one embodiment consistent with the present invention.

Once the procedure is completed and all registration data recorded in the database, the device is activated in step 900 (see FIG. 9). Once activated the embedded diagnostic biosensors within the device begin collecting and recording data in real time (step 901), in accordance with the predefined instructions related to the frequency and type of data collection along with expected data ranges of "normalcy".

As new data is collected and recorded in step 901, a data profile is created for each different type of sensor embedded within the medical device in step 902, which effectively defines the expected two standard deviations of data measurements. Routinely, the corresponding high and low data values within this range would define "data outliers' (step 903), which would automatically trigger further action and/or analysis by the program in step 906 (see below). The range of data "normalcy" can be defined by the clinical and/or technology providers (based upon specific patient or technology attributes), which create rules as to what data is defined as abnormal and requires further action.

In addition to ongoing collection and analysis of sensor derived data, additional data recorded in the medical device database regarding pre-existing patient or technology risk factors or concomitant disease may be correlated with the sensor derived data by the program in step 904. As an example, if a patient is determined to have a higher than expected risk for systemic or device related infection pre-defined clinical and or laboratory data (e.g., body temperature, white blood cell count) may be included in the medical device database and analyses. Alternatively, if a new infection is discovered during the time of medical device placement which incurs a higher risk for medical device complication (e.g., device infection), these additional clinical/laboratory data elements may be added to the medical database during the period of increased risk.

As diagnostic data is routinely recorded and analyzed (upon transfer to the medical device database), predefined analytics can be performed and automatically sent to authorized end users (e.g., patient, clinical provider) in step 905, in accordance with predefined regimen. The method of data communication and display can be customized to the individual needs and preferences of each individual end-user. While comprehensive data assimilation may be the norm for patients and primary care providers, more detailed data (e.g., individual sensor data) may be requested by more specialized end-users (e.g., surgeon, quality control nurse).

In addition to the sensor derived diagnostic data, sensor quality assurance data (relating to sensor functionality, which is also recorded in step 901) may also be analyzed in step 905 and included in routine reports for those individuals tasked with medical device quality control in step 916. This data is of particular importance to the technology producer, who is tasked with ensuring functionality and integrity of the device and its individual components.

In the event that a data abnormality is detected in step 906 (either diagnostic or sensor quality assurance data), which is beyond two standard deviations from its baseline measures as analyzed by the program, it is important to differentiate between abnormal data due to an underlying problem or artificially abnormal data due to a temporary data artifact or technical glitch. Before escalating the data notification pathway (step 913), the abnormal data measurement is automatically repeated by the program in step 908 to ensure accuracy, along with the program correlating the abnormal data with comparable measures derived from neighboring sensors in step 909.

If the repeated measurement is consistently abnormal (or worse) than the initial measurement as in step 910, yet not confirmed by neighboring sensors, a quality assurance test of sensor reliability may be performed by the program in step 911, through for example, the release of a well-defined entity (i.e., test dose) from the sensor in question, which is intended to confirm sensor accuracy and calibration.

If these combined quality assurance, repeat measurements, and correlation with neighboring sensors confirm the abnormal data in question in step 912, then an assumption of data abnormality is made by the program, which in turn has the program trigger an automated notification pathway along with increased data surveillance in step 913.

Once the abnormal data has been authenticated and reproduced in step 909, an automated data notification pathway is initiated in step 913 which is defined by the specific type, magnitude, and temporal change of the data abnormality. In order to maintain data standardization, a tiered notification system is employed which defines the severity of the abnormality, notification parties, communication and response time requirements.

In the event that the requisite communication response was not verified in the defined period of time in step 914, an all data relating to data transmission, receipt confirmation, and response are automatically recorded in the medical device database for further analysis (and intervention if required) in step 915.

In parallel to the communication of authenticated abnormal data in step 911, automated database analytics are performed by the program in step 905, which correlate the current data outlier with comparable data (same patient, same sensor) over time, in effect creating a time-activity curve which can be used for decision support and comparative data analysis from other patients.

The magnitude and type of data outlier, technology in use, and sensor location are all cross referenced with "comparable" data (i.e., similar patient, clinical, and technology profiles) in step 907 in order to create a computerized predictor (i.e., using neural networks and other forms of artificial intelligence) of disease probability, severity, and intervention requirements.

Upon receipt of the abnormal sensor derived data and computerized database analytics in step 916, the responsible clinical providers are tasked with determining the optimal intervention response in step 917. This may be as simple as continuing data surveillance at a more robust frequency or as aggressive as removing the medical device in question. Before actual device removal, however, a number of more conservative options are preferred by the user, which have the goals of conservatively managing the underling disease or device deficiency, while maintaining the functionality and intended purpose of the device. While therapeutic options are contemplated, continuous data is collected by the program (step 901) to monitor the extent, progression, and/or severity of disease' in the initially involved and neighboring sensors.

The determination of optimal clinical and/or technical response (step 917) to the abnormal data should be customized to the specific patient, clinical context, and technology in use. The ability of the program to correlate real-time sensor derived data with historical data (including outcomes measures) within the medical database provides a powerful tool for defining treatment options and expected outcomes specific to the individual patient, clinical context, and technology. If for example, one was to search the medical device database for comparable data abnormalities in similar patients and technologies, one could in theory compare the treatment interventions employed and observed clinical outcomes, to determine the optimal course of action (i.e., computerized decision support).

If on the other hand the clinical provider was to select an alternative course of action, he or she could search the database of 'comparable patients" who were treated in a similar manner to get an idea as to the success of this alternative treatment option. Regardless of the strategy used, the medical device database provides an opportunity for the program to leverage historical medical device and clinical outcomes data to plan a customized intervention strategy based upon specific patient, clinical, and technology variables.

Once the intervention strategy has been decided upon and employed in step 917, the relative success or failure of intervention will be readily determined by continuous data measures by the program. These data will be automatically recorded in the medical device database in step 918 for the purposes of continuous patient and device monitoring, outcomes analysis, and technology assessment. Ultimately, these data can be used to create best practice guidelines in step 919 specific to the technology and patient profiles.

This sequence of events in the customary use of the invention is as follows:
1. Procedural and technology assessment
2. Informed consent
3. Device registration
4. Performance of procedure (device placement)
5. Device activation (step 900)
6. Ongoing diagnostic device data collection (step 901)
7. Routine data communication (step 902)
8. Identification and verification of abnormal data (steps 903, 904, 906, 908-910)
9. Sensor diagnostics (quality control) (steps 911, 912)
10. Automated abnormal data notification pathway (step 913)
11. Computerized data analytics (steps 915, 907)
12. Decision Support and therapeutic options (step 916)
13. Intervention and monitoring of treatment response (steps 917-918)

However, the above steps may be in different sequence, or may include some or additional or alternative steps, depending on the specific features required by the user.

The following are examples which are provided for illustrative purposes. In one example, a patient who has undergone spinal fixation surgery has newly identified data abnormality in one of the pedicle screws (see FIG. 6, for example) which is suspicious for loss of device integrity (i.e., screw breakage). Repeat sensor derived data collection and analysis by the program confirms the abnormality in question, its specific device location, interval change over time, and dynamic response to different patient positions and external stressors. By having the ability to query the patient regarding subjective perceptions (e.g., pain) and levels of activity at specific points in time and entering this data into the device database, the objective sensor derived data can be correlated by the program with subjective patient and activity data to provide a dynamic and better understanding of device malfunction and pathophysiology.

In addition to periodic (e.g., every 2 hours) patient inquires requesting feedback related to pain sensation and activity, each time an accentuated sensor derived data measure is recorded, a time stamped inquiry is automatically initiated in an attempt to better gauge causative factors associated with worsening measures of device integrity. In this particular example, three unusually higher than normal measures of device malfunction (e.g., increased rotation and translational pressure at the site of pedicle screw breakage) were recorded over a 5 minute period, suggesting a precipitating event.

Feedback from the patient confirms the presence of increased back pain during the specific time period when increased motion/pressure was detected in the device sensors. The patient reports moving furniture during this specific period of time, which involved twisting, increased flexion, and physical exertion with Valsalva maneuver. In order to better identify the causative factors, the patient was called into the orthopedic surgeon's office and put under a series of provocative tests to measure the pain and sensor responses. At the same time, certain exercises and positions were tested to see if these were helpful in reducing pain and abnormal sensors measures. This collective data was then correlated by the program with the device database, with the program specifically searching for historical records of the same type of medical device, similar disease processes (e.g., grade 2 spondylolisthesis at the L5-S1 level), comparable patient profiles, and abnormal sensor data. Review of this data reveals that this specific type of medical device has a slightly higher incidence of integrity failure than competing devices when used for treatment of L5-S1 spondylolisthesis and the abnormality is of higher incidence in morbidly obese patients who perform occupational or exercise induced heavy lifting or rapid twisting motions.

Historical outcomes analysis by the program of different treatment regimens in these patients reveals two primary forms of therapy. These include intensive physical therapy aimed at strengthening lower back muscle groups and surgical intervention in the form of device replacement. Given the fact that the sensor derived data abnormalities show the loss of device integrity to be localized to a single pedicle screw (left L5 screw) and the abnormality has not reached critical levels to date (when correlated with the comparable data measures of similar historical patients who required surgical intervention), a conservative approach was chosen.

During the course of physical therapy, continuous sensor data was correlated by the program with the various exercises employed, and long term temporal sensor measures were analyzed by the program in an attempt to gauge the effects of the physical therapy regimen on device stability. Unfortunately as time progressed, the sensor derived measures worsened, and now revealed a new area of device integrity loss (right L5 screw). As the patient's pain symptoms also worsened, the orthopedic surgeon determined that an alternative treatment was required. The conventional surgical alternative would include surgical revision of the hardware which constitutes a major surgical procedure fraught with significant morbidity and a prolonged recovery time.

The present invention however provides an alternative and novel approach to device stabilization, which is currently not available. By utilizing the superficially located reservoir in the medical device, a CT guided injection of methyl methacrylate can be performed, which provides for local delivery of a stabilization agent which can effectively act as bone cement. Utilizing the described internal architecture of the device (with an internal communication network between the reservoir and individual sensors (in side plate) within the device), the methyl methacrylate can be selectively distributed to the individual sensors located at the points of device breakage. In turn, the reservoirs of these individual biosensors can store the methyl methacrylate for selective injection. The timing and volume of injected methyl methacrylate can be selectively optimized in accordance with the size and location of the deficit. Over time, the subsequent sensor measures can provide objective data as to the treatment response and requirement for repeat injection.

All related medical device data is recorded by the program in the master device database, which in turn can be anonymized and useful for scientific research, outcomes analysis, creation of best practice guidelines, personalized medicine, and technology assessment and refinement. Technology vendors and regulatory agencies can directly benefit from this anonymized data which can be sorted in accordance with the specific type of technology used, clinical applications, and patient/provider profiles. In this particular example, the collection of large sample size data can demonstrate to the device manufacturer that the device in question has a higher propensity to develop loss of integrity among certain patient profile groups and at a specific device location (i.e., interface of L5 pedicle screws with surgical plate). The technology vendor and/or regulatory agency can in turn utilize this data in a number of ways with the goal of improving device performance and clinical outcomes:

1. Increase number of sensors in the specific locations of higher loss of integrity.
2. Please a warning to providers to minimize usage of the device in the patient profile groups of higher risk.
3. Modify the device construction to fortify the region of higher breakage.
4. Test new metal alloys for use in the device for enhanced device strengthening and integrity.
5. Create additional education and training tools for surgical providers who exhibit higher levels of device failure to technically improve device deployment and diminish long term post-operative complications.

Note that any of these interventional strategies can be directly measured over time to objectively analyze cause and effect, based on pre and post device data collection and analysis.

In conclusion, MEMS and NEMS based technologies create new and expanded opportunities for early medical diagnosis through the direct incorporation of biosensors into medical devices, commensurate with device technology, functionality, architecture, and clinical use. These technologies also provide the opportunity for early and local intervention related to disease and device failure. Included in the various therapeutic interventions is expanded drug delivery, which is possible through existing and developing microfluidic technologies. Through the integration of biosensor and microprocessor technologies, medical device induced drug delivery can be customized in accordance with desired release time, volume, rate, and method of release (e.g., periodic, continuous, pulsatile drug delivery).

The combination of diagnostic and therapeutic sensors embedded within medical devices creates a unique opportunity for the creation and recording of standardized real-time data and analysis. This data can in turn be used to create standardized referenceable medical device databases which can track and analyze data in accordance with technology, disease, and patient attributes. Multi-institutional data can in turn be comingled to create large sample sized statistics; which can be used in the creation of customizable best practice guidelines, clinical and technical decision support, automated data analytics, and evidence based medicine (EBM) standards. Equally important to this inter-observer analysis is the ability to perform intra-observer analysis; in which longitudinal data from a given patient and medical device is tracked over time to identify early and verifiable temporal changes from baseline, thereby providing the opportunity for early diagnosis and treatment. When interventional therapy is performed, continuous diagnostic data can be used to quantitatively measure therapeutic response, which can be used to customize and refine therapeutic regimens specific to the patient and underlying pathology.

Through the integration of device embedded sensors with information and communication technologies, wireless communication and sensor networks can be created. This provides real-time communication of in vivo medical and technical data to (and between) patients and clinical providers to effect more timely medical care delivery. All communications and data access are in turn recorded in the medical device database, providing a method for safeguarding and ensuring accuracy of data delivery and sharing. The ultimate goal is to improve accountability throughout the continuum of healthcare delivery, while using advanced technology and data to facilitate early and customizable diagnosis and treatment.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A medical device comprising:
a biosensor having a plurality of embedded sensors disposed within at least an outer and inner wall of said biosensor; and
a reservoir disposed between said inner and said outer wall of said biosensor, and which stores one of a specimen or a therapeutic agent;
wherein said biosensor is disposed in a body of a patient; and
wherein said plurality of embedded sensors include at least one of a diagnostic sensor or a therapeutic sensor.

2. The medical device of claim 1, wherein said diagnostic sensor records data with respect to at least one of a structural integrity of said biosensor, chemical or cellular data, flow dynamics, or ultrasound data.

3. The medical device of claim 1, wherein said therapeutic sensor records data with respect to contents of said reservoir.

4. The medical device of claim 3, wherein said biosensor is includes a plurality of biosensors at one or more ends of said biosensor.

5. The medical device of claim 3, wherein said biosensor wireles sly communicates data from said at least one of said therapeutic sensor or said diagnostic sensor to a database of said at least one external data receiving device;
wherein said external data receiving device is at least one of a handheld storage device or a computer system.

6. The medical device of claim 1, further comprising:
a needle which accesses said reservoir.

7. The medical device of claim 6, further comprising:
an external pump; and
an external reservoir.

8. The medical device of claim 1, wherein said biosensor is mobile within the body of the patient.

9. The medical device of claim 1, further comprising:
a guidance locking system disposed in an outer wall of said biosensor.

\* \* \* \* \*